United States Patent
Priori et al.

(10) Patent No.: US 11,591,602 B2
(45) Date of Patent: Feb. 28, 2023

(54) METHOD OF ALLELE SPECIFIC SILENCING FOR THE TREATMENT OF AUTOSOMAL DOMINANT CATECHOLAMINERGIC POLYMORPHIC VENTRICULAR TACHYCARDIA (CPVT)

(71) Applicant: Istituti Clinici Scientifici Maugeri SpA SB, Pavia (IT)

(72) Inventors: Silvia G. Priori, Milan (IT); Rossana Bongianino, Cura Carpignano (IT); Marco Denegri, Stradella (IT); Carlo Napolitano, Milan (IT)

(73) Assignee: Istituti Clinici Scientifici Maugeri SpA SB, Pavia (IT)

( * ) Notice: Subject to any disclaimer, the term of this patent is extended or adjusted under 35 U.S.C. 154(b) by 558 days.

(21) Appl. No.: 16/077,835

(22) PCT Filed: Feb. 14, 2017

(86) PCT No.: PCT/IB2017/050809
§ 371 (c)(1),
(2) Date: Aug. 14, 2018

(87) PCT Pub. No.: WO2017/141157
PCT Pub. Date: Aug. 24, 2017

(65) Prior Publication Data
US 2021/0189401 A1 Jun. 24, 2021

Related U.S. Application Data

(60) Provisional application No. 62/295,168, filed on Feb. 15, 2016.

(51) Int. Cl.
*C12N 15/11* (2006.01)
*C12N 15/113* (2010.01)
*A61P 9/00* (2006.01)
*A61K 9/127* (2006.01)
*C12N 15/86* (2006.01)

(52) U.S. Cl.
CPC .......... *C12N 15/1138* (2013.01); *A61K 9/127* (2013.01); *A61P 9/00* (2018.01); *C12N 15/1136* (2013.01); *C12N 15/1137* (2013.01); *C12N 15/86* (2013.01); *C12N 2310/14* (2013.01); *C12N 2310/315* (2013.01); *C12N 2310/321* (2013.01); *C12N 2310/322* (2013.01); *C12N 2320/32* (2013.01); *C12N 2320/34* (2013.01); *C12N 2750/14043* (2013.01); *C12N 2750/14071* (2013.01)

(58) Field of Classification Search
CPC ................ C12N 15/1138; C12N 15/86; C12N 2310/14; C12N 2310/315; C12N 2310/321; C12N 2310/322; A61K 9/127
See application file for complete search history.

(56) References Cited

U.S. PATENT DOCUMENTS

| 7,741,529 B1 | 6/2010 | Priori et al. |
| 2013/0197061 A1 | 8/2013 | Hohjoh et al. |

FOREIGN PATENT DOCUMENTS

| WO | WO-2006040357 A2 * | 4/2006 | ......... A61K 31/7088 |
| WO | WO-2011012724 A1 * | 2/2011 | ......... A61K 48/0075 |

OTHER PUBLICATIONS

Hwang et al., "Inhibition of cardiac Ca2+ release channels (RyR2) determines efficacy of class 1 antiarrhythmic drugs in catecholaminergic polymorphic ventricular tachycardia," Circ Arrhythm Electrophysiol. 4(2):128-35 (2011).
Galati et al., "RyR2 QQ2958 Genotype and Risk of Malignant Ventricular Arrhythmias," Cardiol Res Pract. 2016:2868604 (2016) (8 pages).
Guo et al., "RNAi targeting ryanodince receptor 2 protects rat cardiomyocytes from injury caused by simulated ischemia-reperfusion," Biomed Pharmacother. 64(3):184-190 (2010).
Zhou et al., "Ryanodine receptor 2 contributes to hemorrhagic shock-induced bi-phasic vascular reactivity in rats," Acta Pharmacol Sin. 35(11):1375-1384 (2014).
International Search Report and Written Opinion dated May 15, 2017 for Priori, "Method of allele specific silencing for the treatment of autosomal dominant catecholaminergic polymorphic ventricular tachycardia (cpvt)," International Patent Application No. PCT/IB2017/050809, filed Februrary 14, 2017 (13 pages).
Notice of Reasons for Rejection for Japanese Patent Application No. 2018-561101, dated Apr. 6, 2021 (7 pages).

* cited by examiner

*Primary Examiner* — Ekaterina Poliakova-Georgantas
(74) *Attorney, Agent, or Firm* — Clark & Elbing LLP

(57) ABSTRACT

The present invention provides a method for the treatment of autosomal dominant Catecholaminergic Polymorphic Ventricular Tachycardia associated with mutations in the cardiac ryanodine receptor type 2 (RYR2) gene, by the use of an AAV mediated RNA interference approach to induce allele specific silencing of mutant mRNA.

16 Claims, 14 Drawing Sheets

Specification includes a Sequence Listing.

METHOD OF ALLELE SPECIFIC SILENCING FOR THE TREATMENT OF AUTOSOMAL DOMINANT CATECHOLAMINERGIC POLYMORPHIC VENTRICULAR TACHYCARDIA (CPVT)

FIELD OF THE INVENTION

The present invention concerns a method for the treatment of autosomal dominant Catecholaminergic Polymorphic Ventricular Tachycardia, associated with mutations in the cardiac ryanodine receptor type 2 (RYR2) gene, by the use of an AAV mediated RNA interference approach to induce allele specific silencing of mutant mRNA.

STATE OF THE ART

Catecholaminergic Polymorphic Ventricular Tachycardia (CPVT) is an inherited channelopathy characterized by high susceptibility to life threatening arrhythmias. Two forms of the disease have been described: the autosomal dominant and the autosomal recessive variant. The first is associated with mutations in the cardiac ryanodine receptor type 2 (RYR2) gene (Priori S G et al., 2001), while the autosomal recessive variant is associated with mutations in the cardiac calsequestrin 2 (CASQ2) gene (Lahat H et al., 2001). Clinical observations have shown that patients with the dominant form of CPVT develop bidirectional and polymorphic ventricular tachycardia in response to sympathetic activation, whereas their resting ECGs are unremarkable and heart structure is preserved. The response to current therapy is unable to effectively reduce sudden death in affected individual and therefore there is need for an innovative treatment able to correct all aspects of the functional derangements observed in the dominant form of CPVT.

The pathology is linked to an abnormal function of the physiologic mechanism called 'calcium-induced calcium release' (CICR) that is the fundamental for the excitation-contraction coupling in the heart.

The highly coordinated opening and closing of voltage-dependent ion channels located in the membrane of cardiac myocytes generates the cardiac action potential. During the plateau phase of the action potential, opening of voltage-dependent L-type $Ca^{2+}$ channels allows the influx of $Ca^{2+}$ in the plasmalemma. This process triggers the calcium transient and induces opening of sarcoplasmic reticulum (SR) $Ca^{2+}$ release channels: the ryanodine receptor 2 (RyR2) (Bers D M, 2002). These local releases occur at specialized structures called the calcium release units (CRUs). The CRUs are preferentially localized at the level of the transverse tubules (T-tubules), where the membrane of the SR is juxtaposed to the cellular membrane. One CRU is formed by clusters of RyR2 (spanning the SR membrane) that are in close proximity to the L-type $Ca^{2+}$ channels (on the cell membrane) (Franzini-Armstrong et al., 2005). The $Ca^{2+}$ released from the SR binds to troponin C and induces a series of allosteric changes in the myosin filaments leading to muscle fiber contraction. The subsequent removal of $Ca^{2+}$ is mediated by the concomitant closing of the RyR2 and the action of SR $Ca^{2+}$ ATPase (SERCA) that pumps $Ca^{2+}$ back into the SR stores.

Another component of $Ca^{2+}$-transient termination is the $Na^+$—$Ca^{2+}$ exchanger (NCX). The NCX extrudes one $Ca^{2+}$ ion (two positive charges) for every three $Na^+$ ions (three positive charges) taken into the cell. Thus, the NCX removes $Ca^{2+}$ by generating a net inward depolarizing current: the transient inward current (Iti) (Pieske B et al., 1999). The NCX becomes very important for the removal of $Ca^{2+}$ in conditions characterized by calcium overload, for example in case of RYR2 genetic mutations.

Arrhythmias in CPVT are elicited by $Ca^{2+}$ release events that are not triggered by an action potential and are, therefore, called 'spontaneous calcium releases' (SCRs). SCR begins as a localized event involving a single CRU, but can also diffuse to neighboring CRUs triggering more $Ca^{2+}$ release to produce a cell-wide calcium wave. The probability that SCR will lead to a calcium wave is influenced by the balance between SR $Ca^{2+}$ content and the concentration of $Ca^{2+}$ that induces $Ca^{2+}$ release from the SR, the so-called SR calcium threshold. RyR2 function has a pivotal role in controlling the threshold. Several RYR2 mutations associated with CPVT decrease the SR threshold for the release of calcium from the SR and therefore they facilitate the occurrence of Spontaneous Calcium Release (Venetucci L et al., 2012).

When abnormal $Ca^{2+}$ release occurs, cytosolic $Ca^{2+}$ concentration transiently increases and the cell must activate mechanisms to prevent disruption of $Ca^{2+}$ homeostasis and re-establish the physiological diastolic level of $Ca^{2+}$. Extrusion of $Ca^{2+}$ through the NCX is the preferred modality to reduce cytosolic $Ca^{2+}$ however to extrude 1 $Ca^{2+}$ the NCX brings inside the cell 3 Na+ thus creating a net inward current called Transient Inward Current or Iti. This current produces a transient membrane depolarizations known as delayed afterdepolarization (DAD). When a DAD's amplitude reaches the voltage threshold for the opening of the voltage dependent $Na^+$ channel, a 'triggered' action potential is generated. Propagation of an action potential to the entire heart generates an extrasystolic beat. When this chain of events becomes repetitive and several DADs reach the threshold for the generation of propagating action potentials, triggered arrhythmic activity is elicited and it generates complex and life threatening arrhythmias. Mutations of RYR2 have been shown to facilitate the occurrence of Spontaneous Calcium Releases during β-adrenergic stimulation and, in turn, elicit DADs and triggered activity leading to severe ventricular arrhythmias (Liu N et al., 2006).

The generation and characterization of $RyR2^{R4496C/+}$ knock-in mouse model for autosomal dominant CPVT (Cerrone M et al., 2005; Patent: U.S. Pat. No. 7,741,529 B1) has provided great insight into the pathogenic mechanisms underlying this disease. $RyR2^{R4496C/+}$ heterozygous mice recapitulate human CPVT and develop adrenergically induced bidirectional and polymorphic ventricular arrhythmias. R4496C mutation increases the sensitivity of RyR2 channel to luminal calcium thus facilitating the spontaneous release of calcium from the Sarcoplasmic Reticulum. Spontaneous calcium release begins as a localized event involving a single CRU, however it may also propagate to neighboring CRUs triggering more $Ca^{2+}$ release to produce a cell-wide calcium wave. The probability that SCR will lead to a calcium wave is influenced by the balance between SR $Ca^{2+}$ content and the concentration of $Ca^{2+}$ that induces $Ca^{2+}$ release from the SR, the so-called SR calcium threshold. RyR2 function has a pivotal role in controlling the threshold.

SUMMARY OF THE INVENTION

The present invention concerns a method for the treatment of autosomal dominant Catecholaminergic Polymorphic Ventricular Tachycardia through silencing sequences that allow to differentiate the normal allele from the diseased allele of the RyR2 gene.

The method for the treatment of autosomal dominant Catecholaminergic Polymorphic Ventricular Tachycardia according to the invention comprises the exploitation of therapeutic post-transcriptional gene-silencing. The inventors have found that, taking advantage of the endogenous RNA interference (RNAi) pathway (Elbashir et al., 2001), through the delivery of an artificial miRNA expressing vector into a cardiac cell, it is possible to selectively suppress the expression of mutant RyR2 mRNA leaving almost unaltered the expression of the wild type RyR2 transcript in order to correct functional derangements observed in $RyR2^{R4496C/+}$ heterozygous subjects.

The development of an RNAi approach involves some risk such as the supraphysiologic expression of interfering RNAs species and the possibility to cause haploinsufficiency of vital genes, as it is precisely RYR2. Nevertheless, through the accurate selection of interfering RNAs sequences and by using suitable AAV serotype, promoter, as well as vector dose, it is possible to achieve an extent of mutated allele gene silencing that is sufficient to elicit the desired effect, i.e. protecting cardiomyocytes against developing adrenergically triggered activity, but not to affect normal cardiac function. In order to achieve this goal, only strong efficient and strictly specific molecules, derived from the initial in vitro screening, are provided for the use in the in vivo experiments.

DETAILED DESCRIPTION OF THE INVENTION

The present invention concerns a method for the treatment of autosomal dominant Catecholaminergic Polymorphic Ventricular Tachycardia associated with RYR2 (NM_023868.2, NM_001035.2) mutations in mouse models or in human patients.

In one embodiment, the invention provides a method of performing allele-specific gene silencing in mouse models or in human individuals affected by dominantly inherited CPVT, by administering to the subject in need thereof a vector carrying an expression cassette containing a promoter operably linked to sequences encoding a double stranded short interfering nucleic acid (siNA), wherein said siNA targets the RYR2 region containing the nucleotide mutation(s) and it is optimized to obtain a high knockdown rate of the mutant mRNA by sequence complementarity, leaving almost unaltered the expression of the wild type RYR2 transcript.

As used herein, siNA molecule denotes a short interfering RNA (siRNA), double-stranded RNA (dsRNA), micro-RNA (miRNA), short hairpin RNA (shRNA) or a circular RNA molecule.

The targeted RYR2 gene sequences may be murine-specific or human-specific. In human CPVT patients, the gene is the human RYR2 (NM_001035.2; coding sequence: SEQ ID NO:1).

In general, the alleles of the RYR2 gene will differ by one up to seven base pairs to be targeted by allele specific silencing.

In addition to using siNA molecules targeting the RYR2 regions, which contain the nucleotide change/s, the inventors have found that common SNPs can be exploited to generate interfering nucleic acids that selectively silence the mutant RYR2 expression. This alternative approach to RYR2 mutant allele-specific silencing is particularly convenient given the large number of different patient-specific disease causing mutations.

Common disease causing mutations in human RYR2 gene include, but are not limited to, R2474S, R4497C, R176Q, P2328S, Q4201R, V4653F, R176Q, T2504M, C2277R, E1724K, A2254V, A2394G, F4020L, E4076K, N4104I, H4108N, H4108Q, G4662S, H4762P, V4771I, P4902S, N4014K, and N4895D.

Common single nucleotide polymorphisms comprise most of the genetic diversity between humans and the RYR2 gene contains single nucleotide polymorphisms that can be separately targeted in one allele or in the other.

In another embodiment, the invention provides a method of performing allele-specific gene silencing in mouse models or in human individuals affected by dominantly inherited CPVT, by administering to the subject in need thereof a vector carrying an expression cassette containing a promoter operably linked to sequences encoding a double stranded short interfering nucleic acid (siNA), wherein said siNA targets common single nucleotide polymorphisms (SNPs) in the coding region of the RYR2 gene and said SNPs co-segregate with the mutations in the same allele or in the opposite, whereby the RYR2 allele in which the mutation is present is silenced, leaving almost unaltered the expression of the wild type RYR2 transcript.

SNPs typing and linkage analysis between the SNPs and the mutation may easily be assessed at the time of genetic screening that is routine in CPVT patients or at the time in which a patient has been advised to be treated with a gene therapy approach.

A bioinformatic assessment of the frequency and distribution of SNPs has been made using the available databases (Exome Variant Server) and a cohort of CPVT patients, to identify SNPs that have a minor allele frequency (MAF) between 30% and 40% and which thereby are relatively common but not too common to result in a high proportion of homozygous carriers of the minor allele, as of course they are not suitable to act as surrogate targets for the mutation as the same sequence at the SNPs site is present on both alleles.

By performing bioinformatics research, three main SNPs have been identified: rs3765097 (c.1359C>T; p.S453S), rs684923 (c.7806C>T; p.H2602H) and rs34967813 (c.8873A>G; p.Q2958R). The MAF for these SNPs according to different data bases is reported in Table 1.

TABLE 1

Information about three common SNPs in the RYR2 coding sequence taken from the Exome Variant Server. They are mostly prevalent in heterozygosity so they represent potential valid targets for allele specific silencing.

| Variant GRCh37 Pos | rs ID | Alleles | MAF (%) (EA/AA/All) | Genes | mRNA Accession # | GVS Function | cDNA Change | Protein Change |
|---|---|---|---|---|---|---|---|---|
| 1:237617757 | rs3765097 | C > T | 39.949/ 32.141/ 48.8068 | RYR2 | NM_001035.2 | coding-synonymous | c.1359C > T | p.(S453=) |

TABLE 1-continued

Information about three common SNPs in the RYR2 coding sequence taken from the Exome Variant Server. They are mostly prevalent in heterozygosity so they represent potential valid targets for allele specific silencing.

| Variant GRCh37 Pos | rs ID | Alleles | MAF (%) (EA/AA/All) | Genes | mRNA Accession # | GVS Function | cDNA Change | Protein Change |
|---|---|---|---|---|---|---|---|---|
| 1:237814783 | rs684923 | C > T | 43.6082/ 48.3406/ 45.0733 | RYR2 | NM_001035.2 | coding-synonymous | c.7806C > T | p.(H2602=) |
| 1:237841390 | rs34967813 | A > G | 30.4163/ 5.2618/ 22.4871 | RYR2 | NM_001035.2 | missense | c.8873A > G | p.(Q2958R) |

It has been estimated that using the three SNPs there would be 70% of heterozygous carriers with at least one of the three SNPs.

To test this estimate, we have performed a targeted analysis in a cohort of 176 patients, genotyped for RYR2 mutation-linked CPVT to quantify the percentage of carriers of these three SNPs. We observed that 138 individuals have at least one of the three variant in heterozygosity while only 38 patients have none of the polymorphisms in heterozygosity.

Therefore, by creating just six specific siNAs—e.g. miRNA—it would be possible to treat patients thereby enabling the allele specific silencing treatment for the vast majority of CPVT patients with RyR2 mutations.

Based on this approach, the following series of siRNA duplexes targeting the specific human nucleotide variants and its wild type counterpart have been designed. The 21-mer oligonucleotides are derived from siRNA duplex sequence that has demonstrated the best silencing potency and selectivity for the specific nucleotide change/s in the in vitro screening.

SNP: rs3765097 p. (S453S)

siRNA Duplexes to Test if Causative Mutation is in Cis with rs3765097 PP21N (SEQ ID NO: 2)
AUUUGCCUAUAGAGUCCGUAAGCCUAAGUCUGCAGGAUCUCAUUGGCUAC
UUC;

(SEQ ID NO: 3)
AUUUGCCUAUAGAGUCCGUAAGUCUAAGUCUGCAGGAUCUCAUUGGCUAC
UUC;

TABLE 2

| name | Seq 5'→3' | 3'overhang |
|---|---|---|
| siS453RYR2-U4 | AAGUCUAAGUCUGCAGGAUCU (SEQ ID NO: 4) | -TT |
| siS453RYR2-U5 | UAAGUCUAAGUCUGCAGGAUC (SEQ ID NO: 5) | -TT |
| siS453RYR2-U6 | GUAAGUCUAAGUCUGCAGGAU (SEQ ID NO: 6) | -TT |
| siS453RYR2-U7 | CGUAAGUCUAAGUCUGCAGGA (SEQ ID NO: 7) | -TT |
| siS453RYR2-U8 | CCGUAAGUCUAAGUCUGCAGG (SEQ ID NO: 8) | -TT |

TABLE 2-continued

| name | Seq 5'→3' | 3'overhang |
|---|---|---|
| siS453RYR2-U9 | UCCGUAAGUCUAAGUCUGCAG (SEQ ID NO: 9) | -TT |
| siS453RYR2-U10 | GUCCGUAAGUCUAAGUCUGCA (SEQ ID NO: 10) | -TT |
| siS453RYR2-U11 | AGUCCGUAAGUCUAAGUCUGC (SEQ ID NO: 11) | -TT |
| siS453RYR2-U12 | GAGUCCGUAAGUCUAAGUCUG (SEQ ID NO: 12) | -TT |
| siS453RYR2-U13 | AGAGUCCGUAAGUCUAAGUCU (SEQ ID NO: 13) | -TT |
| siS453RYR2-U14 | UAGAGUCCGUAAGUCUAAGUC (SEQ ID NO: 14) | -TT |
| siS453RYR2-U15 | AUAGAGUCCGUAAGUCUAAGU (SEQ ID NO: 15) | -TT |
| siS453RYR2-U16 | UAUAGAGUCCGUAAGUCUAAG (SEQ ID NO: 16) | -TT |
| siS453RYR2-U17 | CUAUAGAGUCCGUAAGUCUAA (SEQ ID NO: 17) | -TT |
| siS453RYR2-U18 | CCUAUAGAGUCCGUAAGUCUA (SEQ ID NO: 18) | -TT |

SiRNA Duplexes to Test if Causative Mutation is in Trans with rs3765097

(SEQ ID NO: 19)
AUUUGCCUAUAGAGUCCGUAAGCCUAAGUCUGCAGGAUCUCAUUGGCUAC
UUC;

(SEQ ID NO: 20)
AUUUGCCUAUAGAGUCCGUAAGUCUAAGUCUGCAGGAUCUCAUUGGCUAC
UUC;

TABLE 3

| nome | Seq 5'→3' | 3'overhang |
|---|---|---|
| siS453RYR2-C4 | AAGCCUAAGUCUGCAGGAUCU (SEQ ID NO: 21) | -TT |
| siS453RYR2-05 | UAAGCCUAAGUCUGCAGGAUC (SEQ ID NO: 22) | -TT |
| siS453RYR2-C6 | GUAAGCCUAAGUCUGCAGGAU (SEQ ID NO: 23) | -TT |

TABLE 3-continued

| Name | Seq 5'→3' | 3'overhang |
|---|---|---|
| siS453RYR2-C7 | CGUAAGCCUAAGUCUGCAGGA (SEQ ID NO: 24) | -TT |
| siS453RYR2-C8 | CCGUAAGCCUAAGUCUGCAGG (SEQ ID NO: 25) | -TT |
| siS453RYR2-C9 | UCCGUAAGCCUAAGUCUGCAG (SEQ ID NO: 26) | -TT |
| siS453RYR2-C10 | GUCCGUAAGCCUAAGUCUGCA (SEQ ID NO: 27) | -TT |
| siS453RYR2-C11 | AGUCCGUAAGCCUAAGUCUGC (SEQ ID NO: 28) | -TT |
| siS453RYR2-C12 | GAGUCCGUAAGCCUAAGUCUG (SEQ ID NO: 29) | -TT |
| siS453RYR2-C13 | AGAGUCCGUAAGCCUAAGUCU (SEQ ID NO: 30) | -TT |
| siS453RYR2-C14 | UAGAGUCCGUAAGCCUAAGUC (SEQ ID NO: 31) | -TT |
| siS453RYR2-C15 | AUAGAGUCCGUAAGCCUAAGU (SEQ ID NO: 32) | -TT |
| siS453RYR2-C16 | UAUAGAGUCCGUAAGCCUAAG (SEQ ID NO: 33) | -TT |
| siS453RYR2-C17 | CUAUAGAGUCCGUAAGCCUAA (SEQ ID NO: 34) | -TT |
| siS453RYR2-C18 | CCUAUAGAGUCCGUAAGCCUA (SEQ ID NO: 35) | -TT | siRNA Duplexes to Test if Causative Mutation is in Cis with rs684923

(SEQ ID NO: 36)
GAUGUUCCAUUAUUAAAUGAACACGCAAAGAUGCCUCUUAAA;

(SEQ ID NO: 37)
GAUGUUCCAUUAUUAAAUGAACAUGCAAAGAUGCCUCUUAAA;

TABLE 4

| Name | Seq 5'→3' | 3'overhang |
|---|---|---|
| siH2602RYR2-U4 | ACAUGCAAAGAUGCCUCUUAA (SEQ ID NO: 38) | -TT |
| siH2602RYR2-U5 | AACAUGCAAAGAUGCCUCUUA (SEQ ID NO: 39) | -TT |
| siH2602RYR2-U6 | GAACAUGCAAAGAUGCCUCUU (SEQ ID NO: 40) | -TT |
| siH2602RYR2-U7 | UGAACAUGCAAAGAUGCCUCU (SEQ ID NO: 41) | -TT |
| siH2602RYR2-U8 | AUGAACAUGCAAAGAUGCCUC (SEQ ID NO: 42) | -TT |
| siH2602RYR2-U9 | AAUGAACAUGCAAAGAUGCCU (SEQ ID NO: 43) | -TT |
| siH2602RYR2-U10 | AAAUGAACAUGCAAAGAUGCC (SEQ ID NO: 44) | -TT |
| siH2602RYR2-U11 | UAAAUGAACAUGCAAAGAUGC (SEQ ID NO: 45) | -TT |

TABLE 4-continued

| Name | Seq 5'→3' | 3'overhang |
|---|---|---|
| siH2602RYR2-U12 | UUAAAUGAACAUGCAAAGAUG (SEQ ID NO: 46) | -TT |
| siH2602RYR2-U13 | AUUAAAUGAACAUGCAAAGAU (SEQ ID NO: 47) | -TT |
| siH2602RYR2-U14 | UAUUAAAUGAACAUGCAAAGA (SEQ ID NO: 48) | -TT |
| siH2602RYR2-U15 | UUAUUAAAUGAACAUGCAAAG (SEQ ID NO: 49) | -TT |
| siH2602RYR2-U16 | AUUAUUAAAUGAACAUGCAAA (SEQ ID NO: 50) | -TT |
| siH2602RYR2-U17 | CAUUAUUAAAUGAACAUGCAA (SEQ ID NO: 51) | -TT |
| siH2602RYR2-U18 | CCAUUAUUAAAUGAACAUGCA (SEQ ID NO: 52) | -TT | siRNA Duplexes to Test if Causative Mutation is in Trans with rs684923

(SEQ ID NO: 53)
GAUGUUCCAUUAUUAAAUGAACACGCAAAGAUGCCUCUUAAA;

(SEQ ID NO: 54)
GAUGUUCCAUUAUUAAAUGAACAUGCAAAGAUGCCUCUUAAA;

TABLE 5

| Name | Seq 5'→3' | 3'overhang |
|---|---|---|
| siH2602RYR2-4 | ACACGCAAAGAUGCCUCUUAA (SEQ ID NO: 55) | -TT |
| siH2602RYR2-05 | AACACGCAAAGAUGCCUCUUA (SEQ ID NO: 56) | -TT |
| siH2602RYR2-C6 | GAACACGCAAAGAUGCCUCUU (SEQ ID NO: 57) | -TT |
| siH2602RYR2-C7 | UGAACACGCAAAGAUGCCUCU (SEQ ID NO: 58) | -TT |
| siH2602RYR2-C8 | AUGAACACGCAAAGAUGCCUC (SEQ ID NO: 59) | -TT |
| siH2602RYR2-C9 | AAUGAACACGCAAAGAUGCCU (SEQ ID NO: 60) | -TT |
| siH2602RYR2-C10 | AAAUGAACACGCAAAGAUGCC (SEQ ID NO: 61) | -TT |
| siH2602RYR2-C11 | UAAAUGAACACGCAAAGAUGC (SEQ ID NO: 62) | -TT |
| siH2602RYR2-C12 | UUAAAUGAACACGCAAAGAUG (SEQ ID NO: 63) | -TT |
| siH2602RYR2-C13 | AUUAAAUGAACACGCAAAGAU (SEQ ID NO: 64) | -TT |
| siH2602RYR2-C14 | UAUUAAAUGAACACGCAAAGA (SEQ ID NO: 65) | -TT |
| siH2602RYR2-C15 | UUAUUAAAUGAACACGCAAAG (SEQ ID NO: 66) | -TT |
| siH2602RYR2-C16 | AUUAUUAAAUGAACACGCAAA (SEQ ID NO: 67) | -TT |

TABLE 5-continued

| Name | Seq 5'→3' | 3'overhang |
|---|---|---|
| siH2602RYR2-C17 | CAUUAUUAAAUGAACACGCAA (SEQ ID NO: 68) | -TT |
| siH2602RYR2-C18 | CCAUUAUUAAAUGAACACGCA (SEQ ID NO: 69) | -TT |

SNP: rs34967813 p. (Q2958R)
siRNA Duplexes to Test if Causative Mutation is in Cis with rs34967813

(SEQ ID NO: 70)
GGAGAACAUUUCCCUUAUGAACAAGAAAUCAAGUUCUUUGCAAAA;

(SEQ ID NO: 71)
GGAGAACAUUUCCCUUAUGAACGAGAAAUCAAGUUCUUUGCAAAA;

TABLE 6

| Name | Seq 5'→3' | 3'overhang |
|---|---|---|
| siQ2958R-RYR2-G4 | AACGAGAAAUCAAGUUCUUUG (SEQ ID NO: 72) | -TT |
| siQ2958R-RYR2-G5 | GAACGAGAAAUCAAGUUCUUU (SEQ ID NO: 73) | -TT |
| siQ2958R-RYR2-G6 | UGAACGAGAAAUCAAGUUCUU (SEQ ID NO: 74) | -TT |
| siQ2958R-RYR2-G7 | AUGAACGAGAAAUCAAGUUCU (SEQ ID NO: 75) | -TT |
| siQ2958R-RYR2-G8 | UAUGAACGAGAAAUCAAGUUC (SEQ ID NO: 76) | -TT |
| siQ2958R-RYR2-G9 | UUAUGAACGAGAAAUCAAGUU (SEQ ID NO: 77) | -TT |
| siQ2958R-RYR2-G10 | CUUAUGAACGAGAAAUCAAGU (SEQ ID NO: 78) | -TT |
| siQ2958R-RYR2-G11 | CCUUAUGAACGAGAAAUCAAG (SEQ ID NO: 79) | -TT |
| siQ2958R-RYR2-G12 | CCCUUAUGAACGAGAAAUCAA (SEQ ID NO: 80) | -TT |
| siQ2958R-RYR2-G13 | UCCCUUAUGAACGAGAAAUCA (SEQ ID NO: 81) | -TT |
| siQ2958R-RYR2-G14 | UUCCCUUAUGAACGAGAAAUC (SEQ ID NO: 82) | -TT |
| siQ2958R-RYR2-G15 | UUUCCCUUAUGAACGAGAAAU (SEQ ID NO: 83) | -TT |
| siQ2958R-RYR2-G16 | AUUUCCCUUAUGAACGAGAAA (SEQ ID NO: 84) | -TT |
| siQ2958R-RYR2-G17 | CAUUUCCCUUAUGAACGAGAA (SEQ ID NO: 85) | -TT |
| siQ2958R-RYR2-G18 | ACAUUUCCCUUAUGAACGAGA (SEQ ID NO: 86) | -TT | siRNA Duplexes to Test if Causative Mutation is in Trans with rs34967813

(SEQ ID NO: 87)
GGAGAACAUUUCCCUUAUGAACAAGAAAUCAAGUUCUUUGCAAAA;

(SEQ ID NO: 88)
GGAGAACAUUUCCCUUAUGAACGAGAAAUCAAGUUCUUUGCAAAA;

TABLE 7

| Name | Seq 5'→3' | 3'overhang |
|---|---|---|
| siQ2958R-RYR2-A4 | AACAAGAAAUCAAGUUCUUUG (SEQ ID NO: 89) | -TT |
| siQ2958R-RYR2-A5 | GAACAAGAAAUCAAGUUCUUU (SEQ ID NO: 90) | -TT |
| siQ2958R-RYR2-A6 | UGAACAAGAAAUCAAGUUCUU (SEQ ID NO: 91) | -TT |
| siQ2958R-RYR2-A7 | AUGAACAAGAAAUCAAGUUCU (SEQ ID NO: 92) | -TT |
| siQ2958R-RYR2-A8 | UAUGAACAAGAAAUCAAGUUC (SEQ ID NO: 93) | -TT |
| siQ2958R-RYR2-A9 | UUAUGAACAAGAAAUCAAGUU (SEQ ID NO: 94) | -TT |
| siQ2958R-RYR2-A10 | CUUAUGAACAAGAAAUCAAGU (SEQ ID NO: 95) | -TT |
| siQ2958R-RYR2-A11 | CCUUAUGAACAAGAAAUCAAG (SEQ ID NO: 96) | -TT |
| siQ2958R-RYR2-A12 | CCCUUAUGAACAAGAAAUCAA (SEQ ID NO: 97) | -TT |
| siQ2958R-RYR2-A13 | UCCCUUAUGAACAAGAAAUCA (SEQ ID NO: 98) | -TT |
| siQ2958R-RYR2-A14 | UUCCCUUAUGAACAAGAAAUC (SEQ ID NO: 99) | -TT |
| siQ2958R-RYR2-A15 | UUUCCCUUAUGAACAAGAAAU (SEQ ID NO: 100) | -TT |
| siQ2958R-RYR2-A16 | AUUUCCCUUAUGAACAAGAAA (SEQ ID NO: 101) | -TT |
| siQ2958R-RYR2-A17 | CAUUUCCCUUAUGAACAAGAA (SEQ ID NO: 102) | -TT |
| siQ2958R-RYR2-A18 | ACAUUUCCCUUAUGAACAAGA (SEQ ID NO: 103) | -TT |
| siQ2958R-RYR2-A19 | AACAUUUCCCUUAUGAACAAG (SEQ ID NO: 104) | -TT |

CLINICAL APPROACH FOR THE APPLICATION OF ALLELE SPECIFIC SILENCING TARGETING SNPs TO SUPPRESS THE MUTANT TRANSCRIPT

Figure 1:
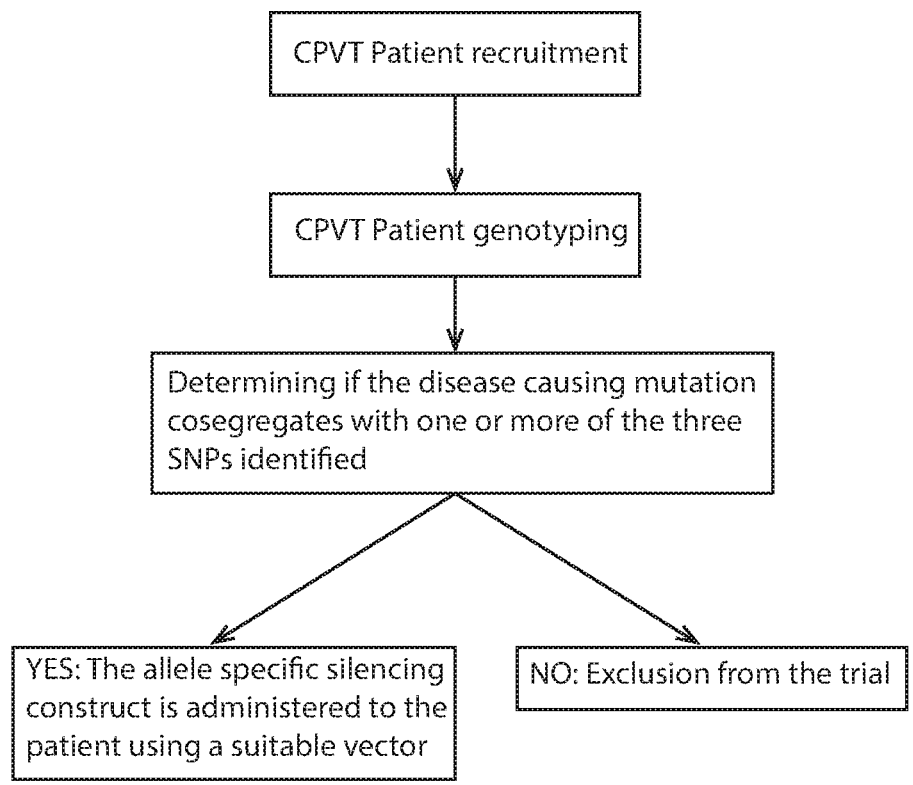
FIG. 1: flow chart depicting the steps that in the clinics will be used to choose the suitable siRNA to silence the allele containing the RyR2 mutation

The flow chart depicting the steps that in the clinics will be used to choose the suitable siRNA to silence the allele containing the RYR2 mutation is shown in FIG. 1.

The therapy will be available in six different products to target the WT or the Mutant variant of each of the 3 SNPs, and siNAs will be developed to target the RNA regions containing the sequences of interest: 1359C; 1359T; 7806C; 7806T; 8873A; 8873G.

Each CPVT patient carrier of a pathogenic mutation in the RYR2 gene who is a candidate for gene therapy through allele specific silencing will be genotyped to determine the co-segregation of the disease causing mutation and the three SNPs.

Once the variant(s) that co-segregate with the mutation is (are) identified, the patient may be suitable to be treated with 1 or 2 or 3 products. The selection of the product to be used will be based on the sequence with the highest selectivity between mutant and WT allele.

In human patients the double-stranded short interfering nucleic acid is targeted to common SNPs including, but not limited to, rs3765097 (c.1359C>T), rs684923 (c.7806C>T) and rs34967813 (c.8873A>G), when they are in heterozygosity, so that they can be used to discriminate the allele carrying the disease causing mutation from the wild-type. This makes possible to generate few siNA sequences that can silence different patient-specific mutations in the RYR2 gene.

In a preferred aspect the engineered pre-siNA (e.g. pre-miRNA) expression cassette is inserted in a vector, preferably into a viral vector. The pre-siNA coding sequence is operably linked to a promoter, which could be CMV, or cardiac specific promoters such as: cTnT, TnC, α-MHC, MLC-2 and other tissue specific promoters.

The engineered pre-siNA expression cassette may be advantageously inserted in the serotype 9 adeno-associated viral (AAV2/9) vector. Alternatively, the engineered pre-siNA expression cassette may be advantageously inserted in the serotype 6 adeno-associated viral (AAV2/6) vector or serotype 8 adeno-associated viral (AAV2/8) vector.

Once the engineered pre-miRNA expression cassette is introduced into the cardiac cells for expression, the pre-miRNA forms an intramolecular stem loop structure similar to the structure of endogenous pre-miRNA that is then processed by the endogenous Dicer enzyme into a mature miRNA (Cullen et al., 2004).

The method according to the present invention allows the correction of the bidirectional and polymorphic arrhythmias in animal models with autosomal dominant CPVT by a viral gene therapy method by which mutant Ryanodine receptor type 2 mRNA is selectively knocked down by an artificially expressed miRNA.

Artificial miRNA expressing vector should be delivered preferably to the cardiac myocytes and expressed, whereby the normal and anti-arrhythmic contractile function of the heart is restored.

In another embodiment, the invention provides a method of in vitro screening of multiple allele-specific siRNA duplexes under heterozygous conditions, comprising co-transfection of two reporter alleles and siRNAs duplexes with known sequence into cultured HEK-293 cells and determining if the mutant allele is substantially silenced while the wild-type allele retains substantially normal expression.

Specifically, the invention provides a method for identifying an siNA capable of selectively silencing a mutant allele of the RYR2 gene compared to the wild-type allele of the RYR2 gene, comprising:

i. co-transfecting HEK-293 cells with mutant and wild-type reporter alleles and a multiplicity of siNA duplexes, ii. determining if the mutant allele is substantially silenced relative to the wild-type allele, and iii. determining the siNA associated with the substantial silencing; thereby identifying the siNA capable of selectively silencing the mutant allele relative to the wild-type allele of the RYR2 gene.

In another preferred aspect, the siNA molecule according to the present invention advantageously allows to prevent or revert structural abnormalities of the CRUs and in the mitochondria that are associated with the R4496C mutation in the RyR2 gene.

EXPERIMENTAL SETTING

In this study, the gene is the murine RyR2 (NM_023868.2) and the targeted nucleotide variant is the C13483T on the protein coding mRNA leading to the R4496C amino acid change in the murine RyR2 protein.

Allele specific targeting study to silence the allele that includes the R4496C mutation in the RYR2 gene.

AAV Mediated RNA Interference Approach to Induce Allele Specific Silencing of Mutant Gene in a RyR2$^{R4496C/+}$ Mouse Model of Catecholaminergic Polymorphic Ventricular Tachycardia 1) Screening Multiple siRNAs in a Transient Expression System Using Reporter Alleles Cellular models were used to test whether it is possible to target mutant allele in a transient expression system. We performed a series of in vitro mRNA and protein based assays to screen multiple potential siRNAs in order to identify siRNAs that would both recognize and efficiently silence the mutated allele preferentially over the wild-type allele.

Figure 2:
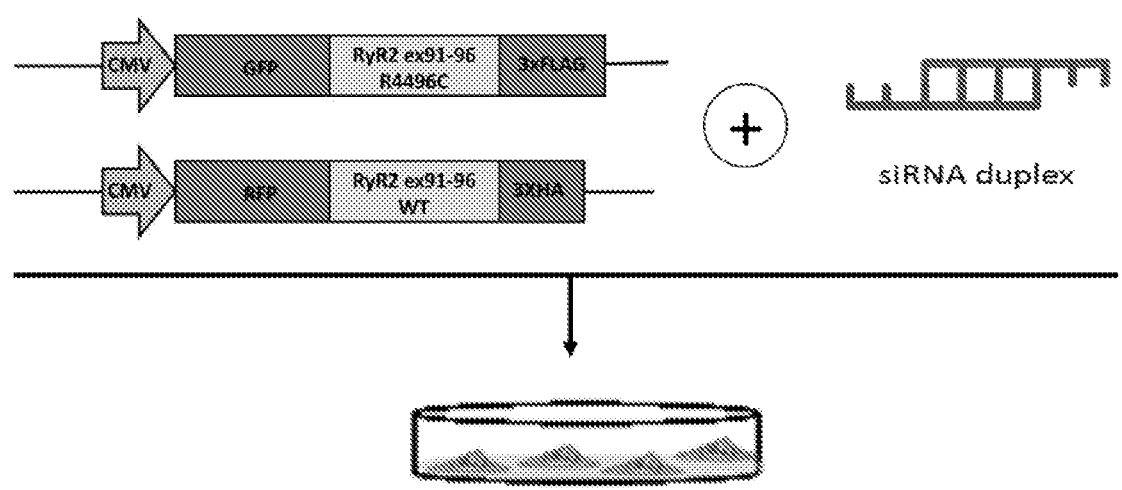
FIG. 2: experimental protocol used to screen multiple siRNA duplexes in transient expression system using reporter alleles to simulate endogenous heterozygous expression of wild type and mutant RYR2 mRNA expression.

Using this system, the effects of a series of siRNA duplexes on mutant alleles in allele-specific silencing, as well as off-target silencing against WT alleles, can be examined under heterozygous conditions generated by co-transfecting two reporter alleles and siRNA duplexes into cultured HEK-293 cells (FIG. 2). As reporter alleles, two plasmids were generated containing:

1) CMV promoter followed by a reporter gene (Red Fluorescent Protein, RFP) in-frame linked with the murine cDNA sequence, corresponding to the WT-mRYR2 (exons 91 to 96), and to a tag sequence (3xHA) (FIG. 2).

2) CMV promoter followed by a reporter gene (Green Fluorescent Protein, GFP) in-frame linked with the murine cDNA sequence, corresponding to the R4496C-mRYR2 (exons 91 to 96), and to a tag sequence (3xFLAG) (FIG. 2).

To induce such allele specific-RNAi, we designed siRNAs that carry nucleotide variations characterizing target disease allele in order to discriminate it from corresponding wild-type allele. Nucleotide sequences of wild-type and mutant RYR2 mRNAs and designed siRNAs are represented below (Table 8) and are based on the sequence of the 5'→3' sense-strand (passenger) siRNA element; mutant recognition site (MRS) is underlined (Table 8).

Wild Type RYR2 mRNA:
(SEQ ID NO: 105)
5'-AACAGAAGCTGCTGAACTATTTTGCTCGCAACTTTTACAACATGAGA ATGCTGGCC-3'

Mutant RYR2 mRNA:
(SEQ ID NO: 106)
5'-AACAGAAGCTGCTGAACTATTTTGCTTGCAACTTTTACAACATGAGA ATGCTGGCC-3'

TABLE 8 sequences of portion of the wild type and mutant RYR2 cDNA and of the tested siRNA duplexes

| name | Seq 5'→3' | 3'overhang |
|---|---|---|
| siRYR2-U5 | UGCUUGCAACUUUUACAACAU (SEQ ID NO: 107) | -TT |
| siRYR2-U6 | UUGCUUGCAACUUUUACAACA (SEQ ID NO: 108) | -TT |
| siRYR2-U7 | UUUGCUUGCAACUUUUACAAC (SEQ ID NO: 109) | -TT |
| siRYR2-U8 | UUUUGCUUGCAACUUUUACAA (SEQ ID NO: 110) | -TT |
| siRYR2-U9 | AUUUUGCUUGCAACUUUUACA (SEQ ID NO: 111) | -TT |
| siRYR2-U10 | UAUUUUGCUUGCAACUUUUAC (SEQ ID NO: 112) | -TT |
| siRYR2-U11 | CUAUUUUGCUUGCAACUUUUA (SEQ ID NO: 113) | -TT |
| siRYR2-U12 | ACUAUUUUGCUUGCAACUUUU (SEQ ID NO: 114) | -TT |
| siRYR2-U13 | AACUAUUUUGCUUGCAACUUU (SEQ ID NO: 115) | -TT |
| siRYR2-U14 | GAACUAUUUUGCUUGCAACUU (SEQ ID NO: 116) | -TT |
| siRYR2-U15 | UGAACUAUUUUGCUUGCAACU (SEQ ID NO: 117) | -TT |
| siRYR2-U16 | CUGAACUAUUUUGCUUGCAAC (SEQ ID NO: 118) | -TT |
| siRYR2-U17 | GCUGAACUAUUUUGCUUGCAA (SEQ ID NO: 119) | -TT |

Figure 3:
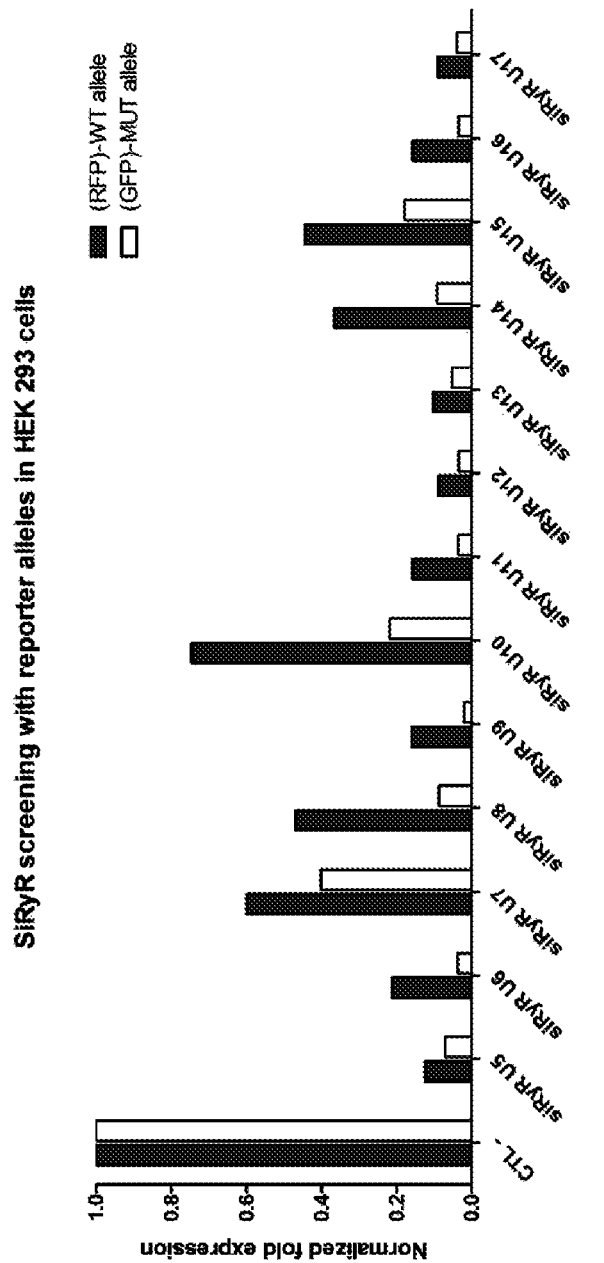
FIG. 3: Assessment of wild type (black) and mutant (white) allele expression by RealTime PCR in Hek293 cells transiently transfected with reporter alleles and siRNA duplexes

2) Assessment of Wild Type and Mutant Allele Expression by RealTime PCR, Fluorescence Microscopy and Western Blot in Transiently Transfected Hek293 Cells The effects of the designed siRNA duplexes on suppression of both the mutant and wild-type alleles have been subsequently examined by RealTime PCR, amplifying with specific primers GFP and RFP gene, to quantify the wild type and mutated allele mRNA respectively (Expression data have been analyzed using the $2^{-\Delta\Delta ct}$ method, normalized on GAPDH expression and relative to the cells treated with scramble siRNA) (FIG. 3).

Most of siRNA duplexes have demonstrated a strong effect in suppressing RYR2 mRNA expression. Moreover, some of them were quite selective for the mutant allele.

Figure 4:
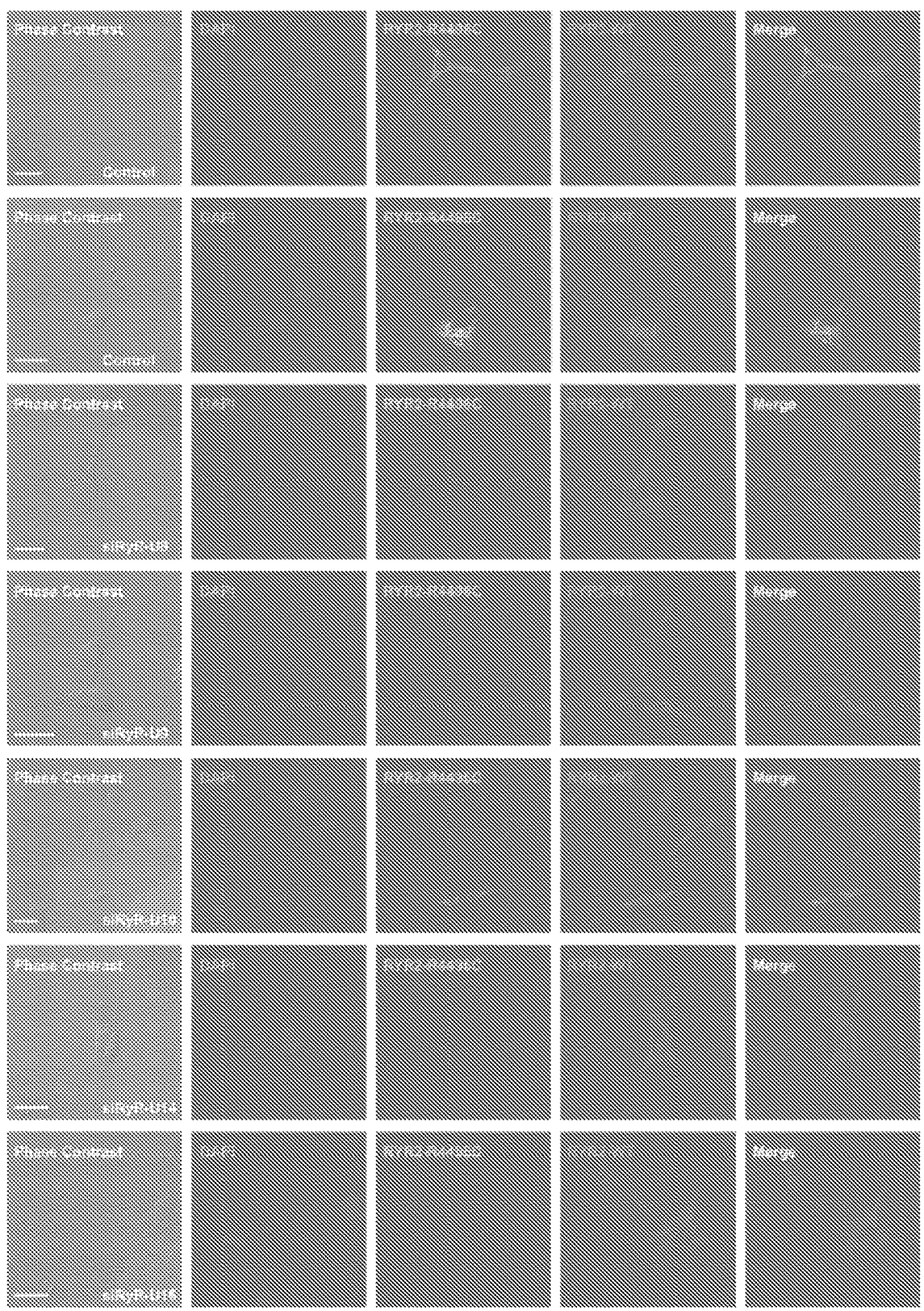
FIG. 4: Fluorescence analysis on in Hek293 cells transiently transfected with reporter alleles and siRNA duplexes
Figure 5:
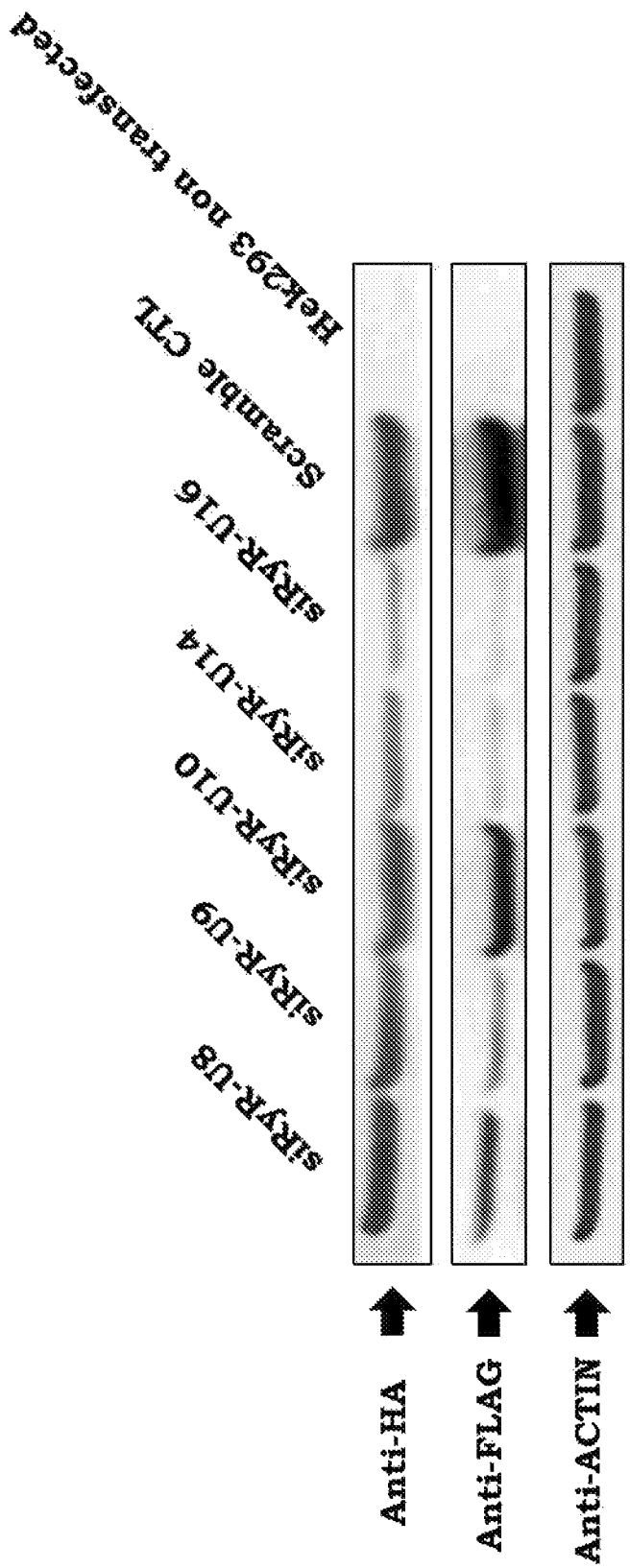
FIG. 5: Western Blot using specific antibody against HA (Wt allele) and FLAG (Mut allele) sequence in Hek293 cells transiently transfected with reporter alleles and siRNA duplexes

Therefore, we choose five siRNAs from this first screening (siRyR-U8, U9, U10, U14 and U16) and deeply analyzed their effect by confocal microscopy, to visualize green and red fluorescence (FIG. 4), and by Western Blot, using specific antibodies anti-HA and -FLAG epitope, to assess the relative protein expression of wild type and mutated allele respectively (FIG. 5).

3) Cloning and Validation of the Candidate siRNA into an Artificial miRNA-Expressing AAV Backbone Plasmid From the previous step we selected siRyR-U10 as the candidate to be cloned into an artificial miRNA expression vector that allows the continuous and long term expression of the silencing molecule.

This siRNA was promising since it induces a weak suppression on the Wild Type allele but a strong silencing on the mutant one.

As an intermediate vector we used the BLOCK-iT™ Pol II miR RNAi Expression Vector (Life Technologies). This vector has a triple advantage over the conventionale Pol III-shRNA expression plasmids:

1. Polimerase II transcribed artificial miRNAs are expressed at tolerability levels while maintaining potent gene silencing capacities compared to shRNA, that can induce toxicity because of their unregulated and massive expression from Pol III promoters.

2. Co-cistronic expression of Emerald GFP (EmGFP), results in correlation of EmGFP expression with knockdown from our mi-RNAi.

3. Strong expression from the CMV immediate early promoter, with the option to use tissue-specific or other regulated promoters (or tissue specific).

Figure 6:
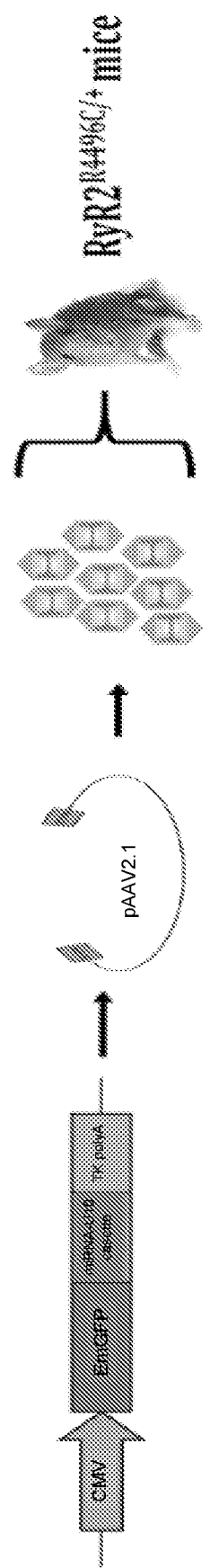
FIG. 6: miRYR2-U10 expression cassette was cloned into the pAAV2.1 adeno associated viral vector backbone plasmid. The resulting plasmid was used for the production of AAV9_miRyR2-U10 particles to infect $RyR2^{R4496C/+}$ heterozygous mice in order to study in vivo the functional effects of the therapy.

Subsequently, a fragment consisting in CMV promoter, EmGFP, pre-miRNA sequence and TKpolyA was amplified from the BLOCK-iT™ Pol II miR RNAi Expression Vector (Life Technologies) and sub-cloned into the adeno associated viral backbone vector pAAV2.1 provided by the Adeno-Associated Virus (AAV) vector Core facility (Tigem, Napoli, Italy) (FIG. 6).

Figure 7:
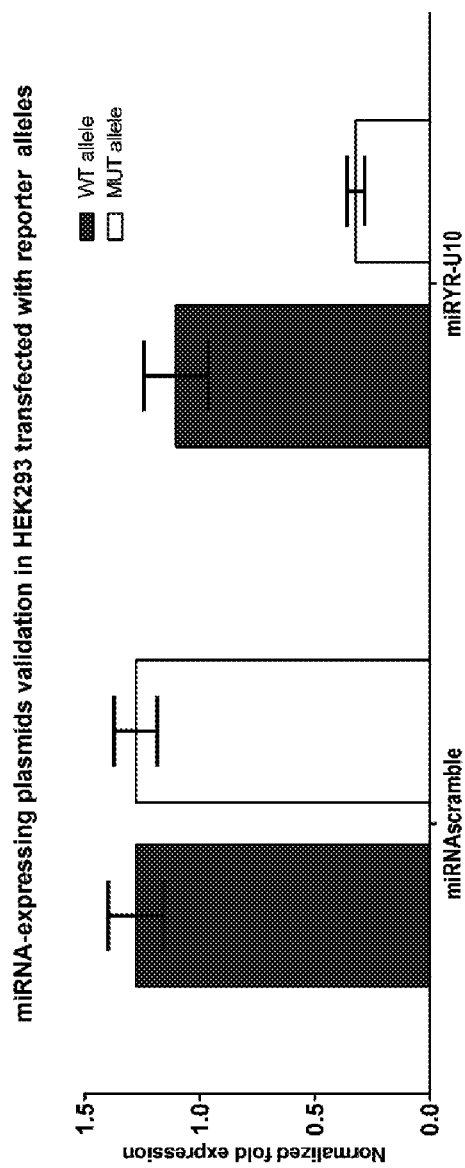
FIG. 7: Assessment of wild type (black) and mutant (white) allele expression by RealTime PCR in Hek293 cells transiently transfected with reporter alleles and pAAV2.1-miRyRU10 or pAAV2.1-miRNAscramble.
Figure 8:
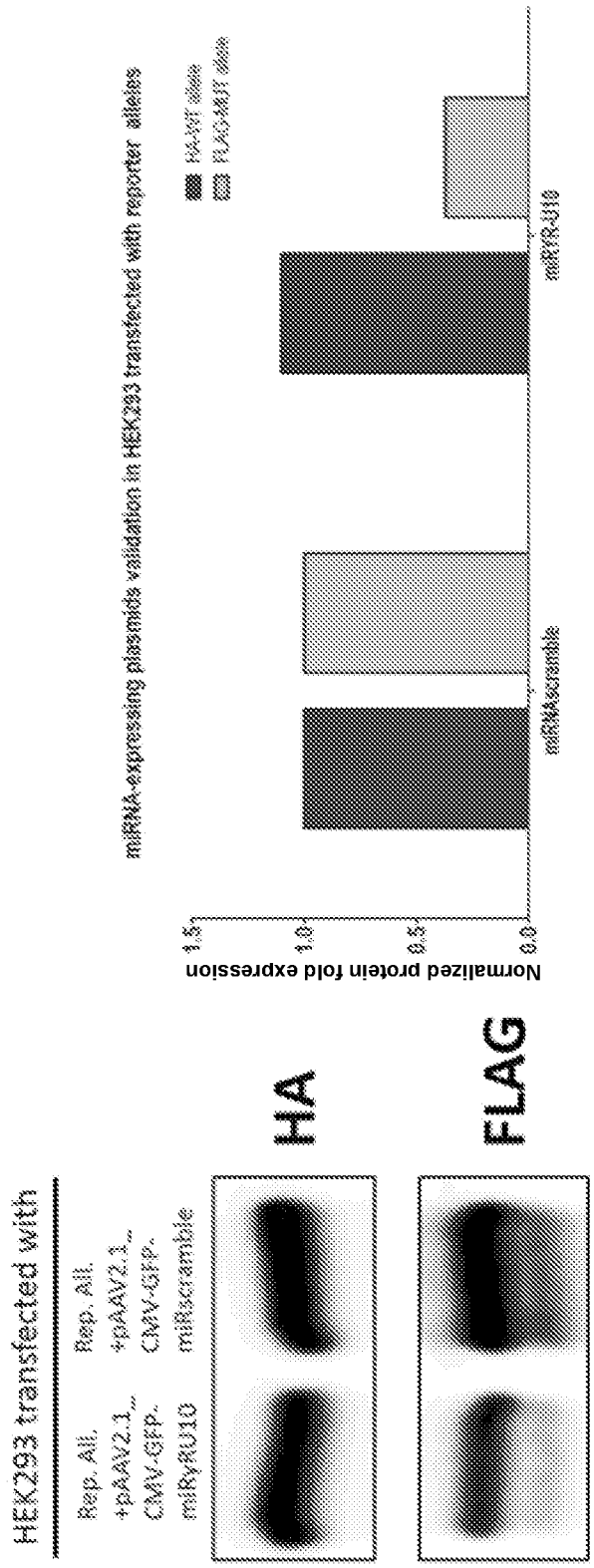
FIG. 8: Western Blot using specific antibody against HA (WT allele) and FLAG (Mut allele) sequence in Hek293 cells transiently transfected with reporter alleles and pAAV2.1-miRyRU10 or pAAV2.1-miRNAscramble.

The resulting plasmid has been validated by RealTime (FIG. 7) and Western Blot (FIG. 8) analysis in the Hek293 cellular system, with heterozygous condition created through the transfection of the two reporter alleles. It was demonstrated that the miRYR2-U10 retains the capacity of siRYR-U10 in substantially suppressing mutant allele expression over the wild type. Expression data were compared to results obtained in cells transfected with reporter alleles and the miRNA-Scramble expressing plasmid (FIGS. 7-8).

Figure 9:
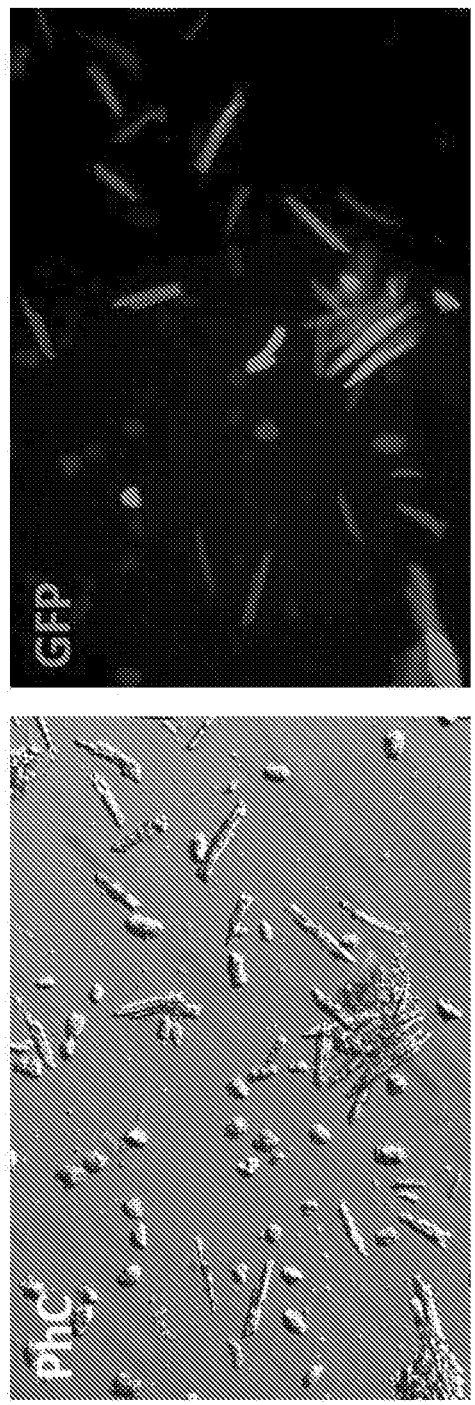
FIG. 9: Isolated cardiomyocytes (Phase Contrast, PhC) from infected animals were observed with fluorescence microscope in order to assess the presence and the level of expression of the reporter gene (EmGFP).

4) In Vivo Infection of Cardiac Murine Myocytes Using the AAV219 Vector for Efficient miRYR2-U10 Transfer We infected, by intraperitoneal (I.P.) injection, neonates (P8/P9 after birth) RyR2$^{R4496C/+}$ heterozygous mice using 100 µl of serotype 9 adeno-associated viral (AAV2/9) vector containing miRYR2-U10 expressing cassette (FIG. 5). The mice were monitored during their development and we did not observe any differences in comparison with the non-infected littermates. To evaluate the infection efficiency in the mice, we performed a standard procedure of cardiac myocytes isolation by enzymatic digestion 8 weeks after infection (4). The isolated cells were plated on coverslips and observed with fluorescence microscope in order to assess the presence and the level of expression of the reporter gene, eGFP (FIG. 9).

5) AAV219-miRYR2-U10 Infection Restores the Functional Phenotype of RyR2$^{R4496C/+}$ Heterozygous Cardiac Cells From our previous investigation we knew that CPVT arrhythmias are caused by delayed after depolarizations (DADs) and triggered activity (TA) at the level of a single cardiomyocyte. Using patch clamp techniques (in current clamp mode) we analyzed the development of the DADs and/or TA in basal condition and after adrenergic stimulation.

Figure 10:
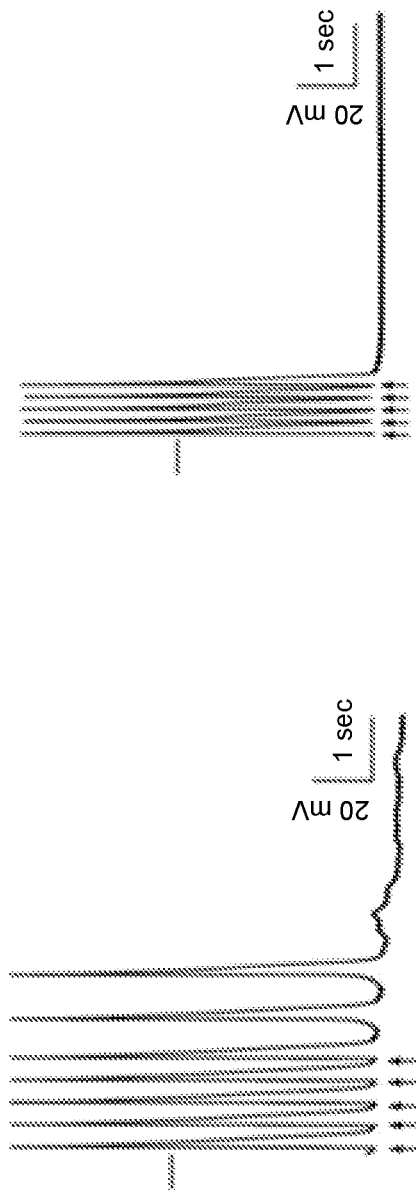
FIG. 10: Examples of triggered activity in isolated cardiomyocytes coming from negative GFP cells (not infected $RYR2-R4496C^{+/-}$ cells) and positive GFP cells (infected $RYR2-R4496C^{+/-}$ cells with AAV2/9-EmGFP-miRYR2)
Figure 10:
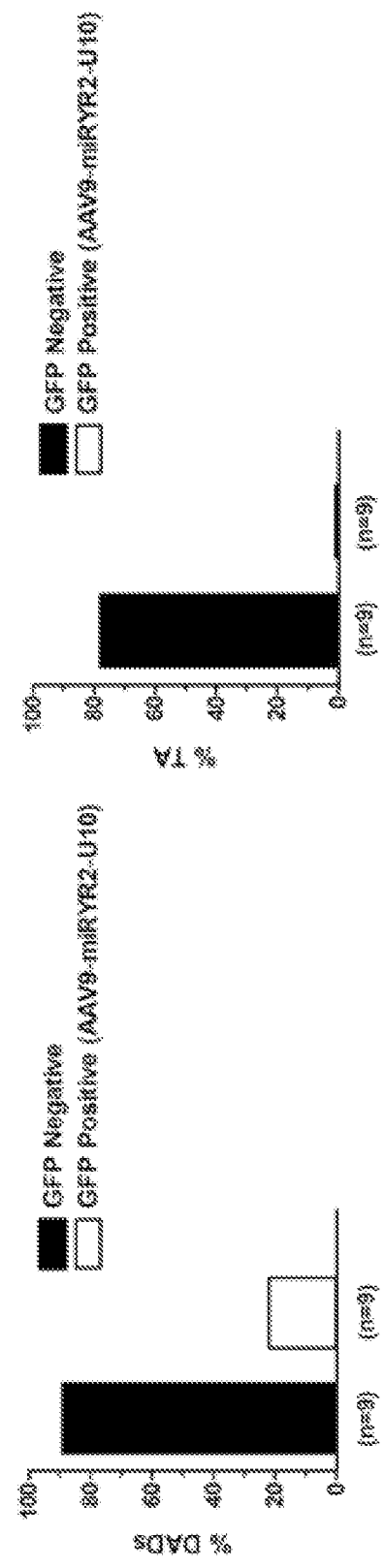

Epifluorescence signal (from the EmGFP present in our viral construct) was used to differentiate between non-infected (i.e. non-fluorescent) and infected (i.e. green fluorescent) cells and to perform comparative assay of DAD and TA occurrence. Isolated myocytes were paced at 5 Hz frequency at 1.5-fold the diastolic threshold and action potential was continuously recorded. An average of 67% of GFP negative (non-fluorescent) cells presented TA after ISO (30 nM) stimulation, while in the same experimental condition, only 6% of the GFP positive infected cells did (FIG. 10).

6) In Vivo Correction of the Dysfunctional Properties Observed in the RyR2$^{R4496C/+}$ mice We used subcutaneous ECG telemeters to monitor and compare the incidence of arrhythmias in resting conditions and during adrenergic stress induced by epinephrine and caffeine injection.

We know from the previous characterization of our autosomal dominant CPVT mouse model that at least 50%-60% of RyR2$^{R4496C/+}$ heterozygous mice present bidirectional ventricular tachycardia during adrenergic stress induced by epinephrine and caffeine injection (Cerrone M et al., 2005). Conversely, when we performed in vivo characterization of the arrhythmogenic substrate in our RyR2$^{R4496C/+}$ heterozygous CPVT mouse model infected with AAV9-miRYR2-U10 we observed that on 10 treated mice only one developed ventricular arrhythmias (10%).

Figure 11:
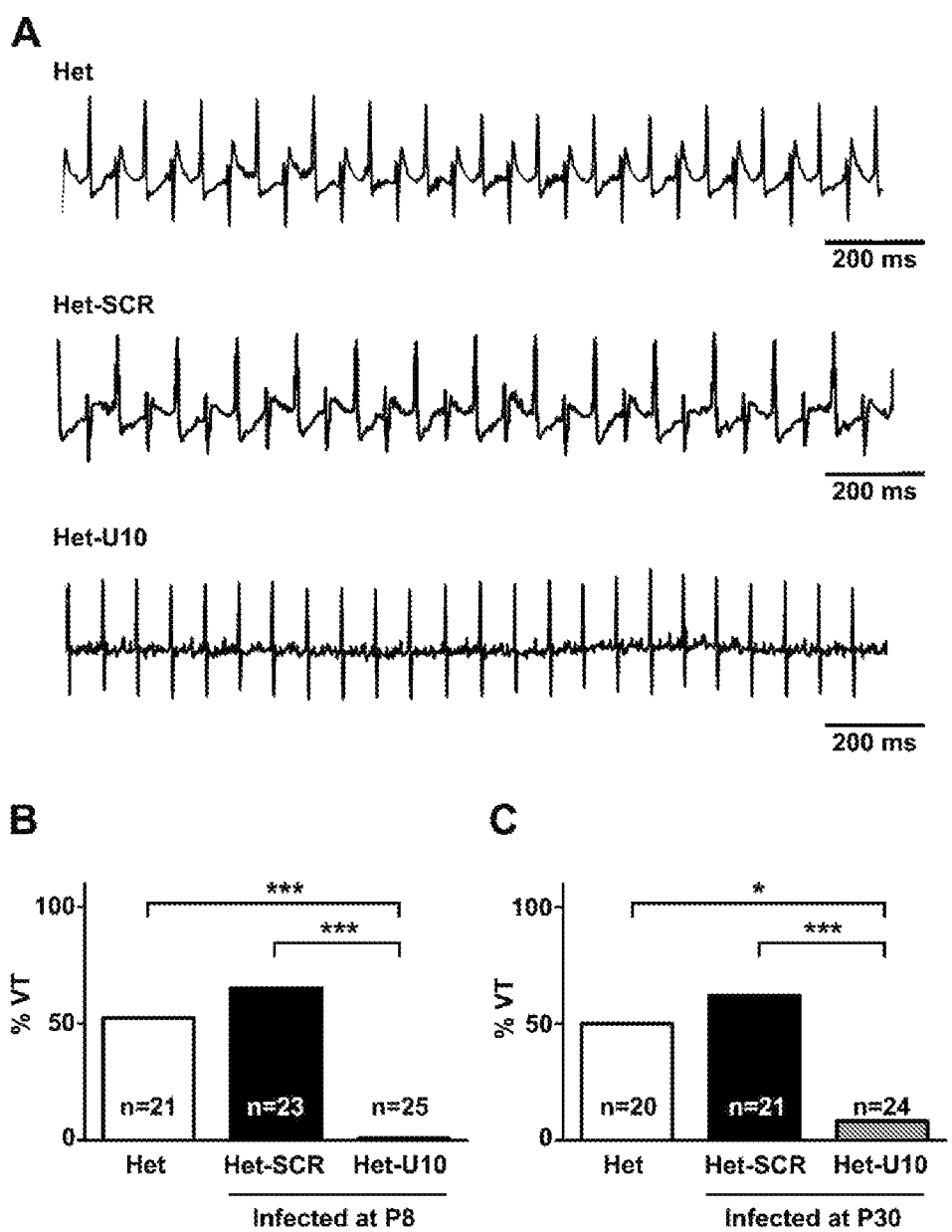
FIG. 11: Evaluation of the incidence of ventricular arrhythmias following allele-specific silencing administration. A, In vivo Epinephrine and Caffeine administration elicited bidirectional ventricular tachycardia in Het and in Het-SCR, but not in Het-U10 mice. B, Quantification of the incidence of ventricular arrhythmias (VT) in Het, Het-SCR and Het-U10 mice infected at p8 (***P<0.001). C, Quantification of the incidence of ventricular arrhythmias (VT) in Het, Het-SCR and Het-U10 mice infected at p30 (*P<0.05; ***P<0.001).

We performed experiments to assess whether administration of the therapeutic construct tested in neonatal mice would also be able to revert the arrhythmic substrate in adult mice. We therefore studied a new set of animals comparing arrhythmic events occurring in 8-week old RyR2$^{R4496C/+}$ heterozygous mice (Het) versus those observed AAV9-miRYR2-U10 (Het-U10) and AAV9-miRNA-Scramble (Het-SCR) infected RyR2$^{R4496C/+}$ heterozygous mice two months after infection (FIG. 11A). Data showed that 52% of Het mice (11/21) and 65% of Het-SCR (15/23) mice exhibited the typical bidirectional ventricular tachycardia, while treatment with miRYR2-U10 completely prevented the development of arrhythmias (0/25; Het-U10 vs Het-SCR *P<0.001; Het-U10 vs Het *P<0.001; FIG. 11B). In vivo evaluation of arrhythmias susceptibility was performed also in 3-months-old mice two months after viral delivery in adult age revealing a remarkable reduction of the ventricular tachycardia occurrence in Het-U10 (2/24, 8%) in comparison with the Het-SCR (13/21, 62%) and Het mice (10/20, 50%; Het-U10 vs Het-SCR ***P<0.001; Het-U10 vs Het *P<0.05; FIG. 11C). This set of data demonstrate that allele specific silencing-based gene therapy not only prevents occurrence of arrhythmic events when administered at birth but also reverts the arrhythmogenic substrate when delivered in post-puberal animals.

7) Morphological Alterations of CRUs in RYR2$^{R4497C/WT}$ Hearts are Rescued by the AAV2/9-miRYR2-U10 Viral Infection.

Figure 12:
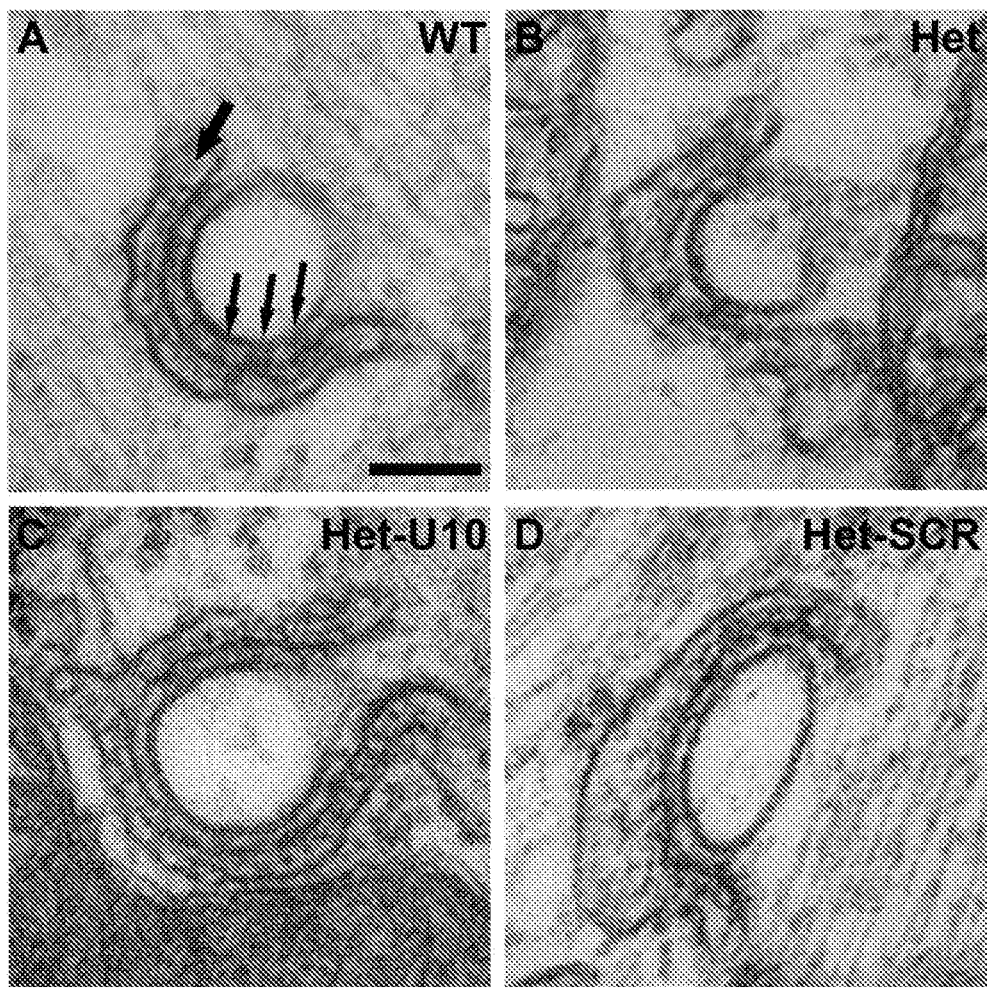
FIG. 12: Electron Microscopy analysis of CRUs in WT and $RyR2^{R4496C/+}$ mice treated with allele specific silencing. A, In WT cardiomyocytes the jSR cisternae are usually narrow and flat. Calsequestrin-2 (CASQ2) is clearly visible as a chain-like electron-dense line that runs parallel to the SR membrane (single black arrow). Smaller arrows in A point to the cytoplasmic domain, or feet, of RYR2s, spanning the narrow junctional gap between SR and plasmalemma. B, In Het cardiomyocytes the shape of jSR is more variable and slightly wider and do not always contain the chain-like electrondense polymer of CASQ2. C, In Het-SCR cardiomyocytes CRUs appear as in Het cardiomyocytes. D, Viral infection in Het-U10 rescues and restore the CRUs profile. Scale bar: 0.1 mm.
Figure 13:
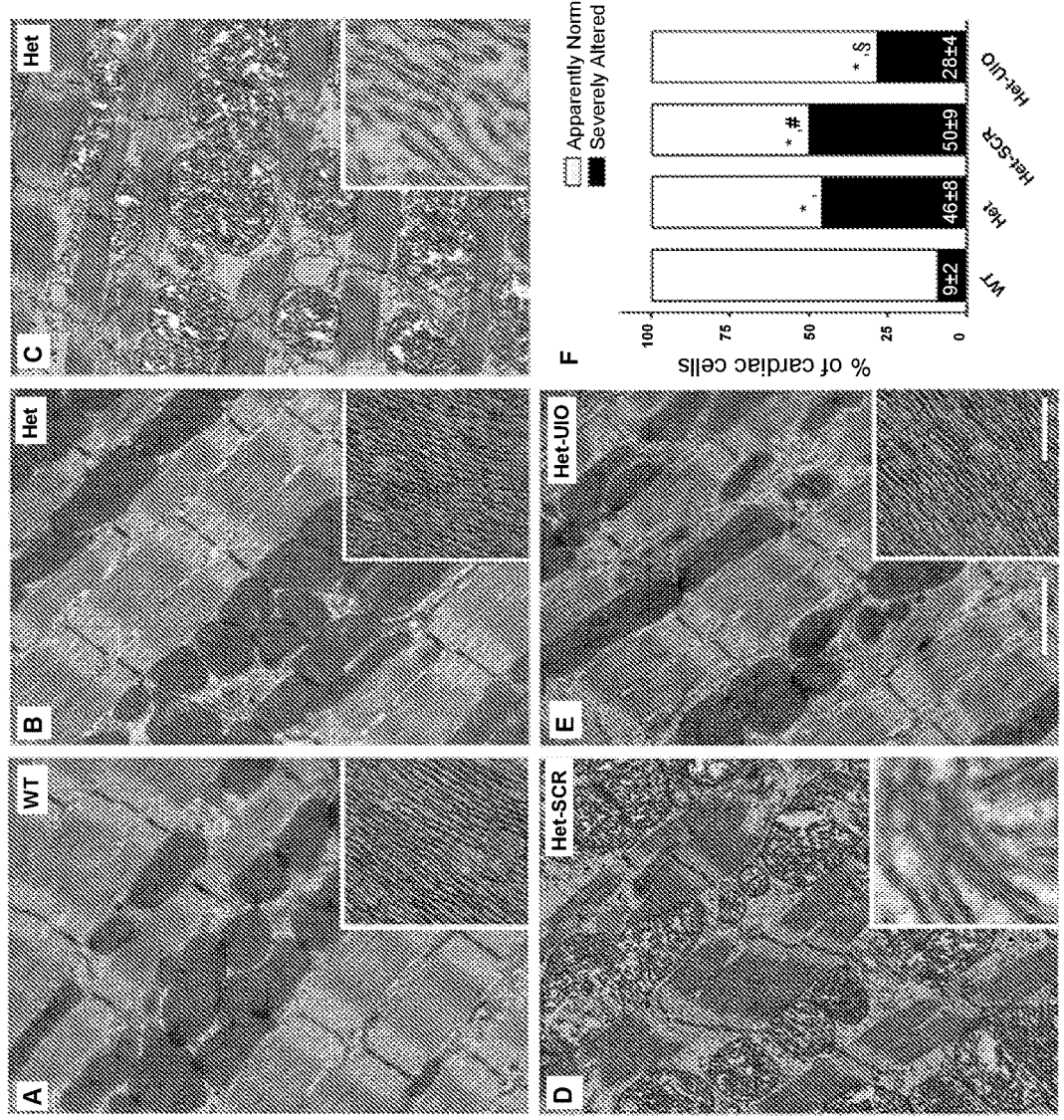
FIG. 13: Electron Microscopy analysis of contractile elements and mitochondria in WT and $RyR2^{R4496C/+}$ mice treated with allele specific silencing. A-E, Representative electron micrographs of cardiac cells in WT (A), Het (B-C), Het-SCR (D) Het-U10 (E). Insets show a detail of mitochondrial internal cristae. F, Quantitative analysis of the percentage of cardiac cells presenting severe structural abnormalities (Het, Het-SCR and Het-U10 vs. WT,*P<0.05; Het-U10 vs. Het, $^§$ P<0.05; Het-SCR vs. Het, $^\#$ not significant). Scale bars=panels A-E, 1 μm; insets, 0.2 μm.

We performed electron microscopy on cardiac tissue of WT and RyR2$^{R4496C/+}$ heterozygous mice to investigate whether in analogy with mice with recessive CPVT (Denegri M et al., 2014) also mice with the dominant form of CPVT present ultrastructural abnormalities and we observed abnormalities in the structure of the calcium release units (CRUs) (FIG. 12). On the surface of the jSR the Ryanodine Receptor channels can be visualized (FIG. 12A, small arrows). In WT cardiomyocytes the jSR cisternae are usually narrow and flat. Calsequestrin-2 (CASQ2) is clearly visible as a chain-like electron-dense line that runs parallel to the SR membrane (FIG. 12A). In RyR2$^{R4496C/+}$ cardiomyocytes the shape of jSR is more variable and slightly wider and do not always contain the chain-like electrondense polymer of CASQ2 (FIG. 12; single black arrow). In cardiomyocytes from RyR2$^{R4496C/+}$ heterozygous mice infected with AAV2/9-miRNA-Scramble (Het-SCR) CRUs appear as in Het cardiomyocytes (FIG. 12D), while viral infection with AAV219-miRYR2-U10 rescues and restore the CRUs profile (Het-U10; FIG. 12C). Interestingly, we observed also that while cardiac samples from WT mice have contractile elements well aligned laterally with each other and mitochondria distributed longitudinally between myofibrils, that exhibit an electron dense matrix with parallel and tightly packed internal cristae (FIG. 13A), approximately 46% of myocytes from heart of Het mice presented damaged mitochondria with increased empty cytoplasmic spaces and alterations of the contractile elements (FIG. 13B-C). Of relevance hearts treated with AAV219-miRYR2-U10 (Het-U10; FIG. 13E), but not those treated with AAV2/9-miRNA-Scramble (Het-SCR; FIG. 13D), showed a reduction in the percentage of cardiac cells with severe mitochondrial abnormalities (from 46% in Het to 28% in Het-U10; FIG. 13F).

8) In Vitro Identification of Allele Specific Silencing Molecules Able to Suppress Expression of Transcripts Containing the rs3765097 (c.1359C>T; p.S453S) or its WT Counterpart in the Human RYR2 Gene.

To transfer the method above described also to the human RYR2 gene and common SNPs that co-segregate with the mutations in the same allele or in the opposite, in a way that the hRYR2 allele in which the mutation is present is silenced, leaving almost unaltered the expression of the wild type RYR2 transcript, we performed a series of in vitro mRNA- and protein-based assays to screen multiple potential siRNAs in order to identify molecules that would both recognize and efficiently silence the SNP containing allele preferentially over the wild-type allele (mimicking the situation in which the SNP is in cis with the mutation) and vice versa (mimicking the situation in which the SNP is in trans with the mutation). The siRNA tested are sequences from SEQ ID NO:4 to SEQ ID NO:18 to target the T-containing allele and from SEQ ID NO:21 to SEQ ID NO:35 to target the C-containing allele.

The effects of tested siRNA duplexes in allele-specific silencing, as well as off-target effects, have been examined under heterozygous conditions generated by co-transfecting two reporter alleles and siRNA duplexes into cultured HEK-293 cells. As reporter alleles, two plasmids were generated containing:

1) CMV promoter followed by a reporter gene (Red Fluorescent Protein, RFP) in-frame linked with the murine cDNA sequence, corresponding to the WT-hRYR2 (exons 11 to 15), and to a tag sequence (3xHA).

2) CMV promoter followed by a reporter gene (Green Fluorescent Protein, GFP) in-frame linked with the murine cDNA sequence, corresponding to the S453S-hRYR2 (exons 11 to 15), and to a tag sequence (3xFLAG).

Figure 14:
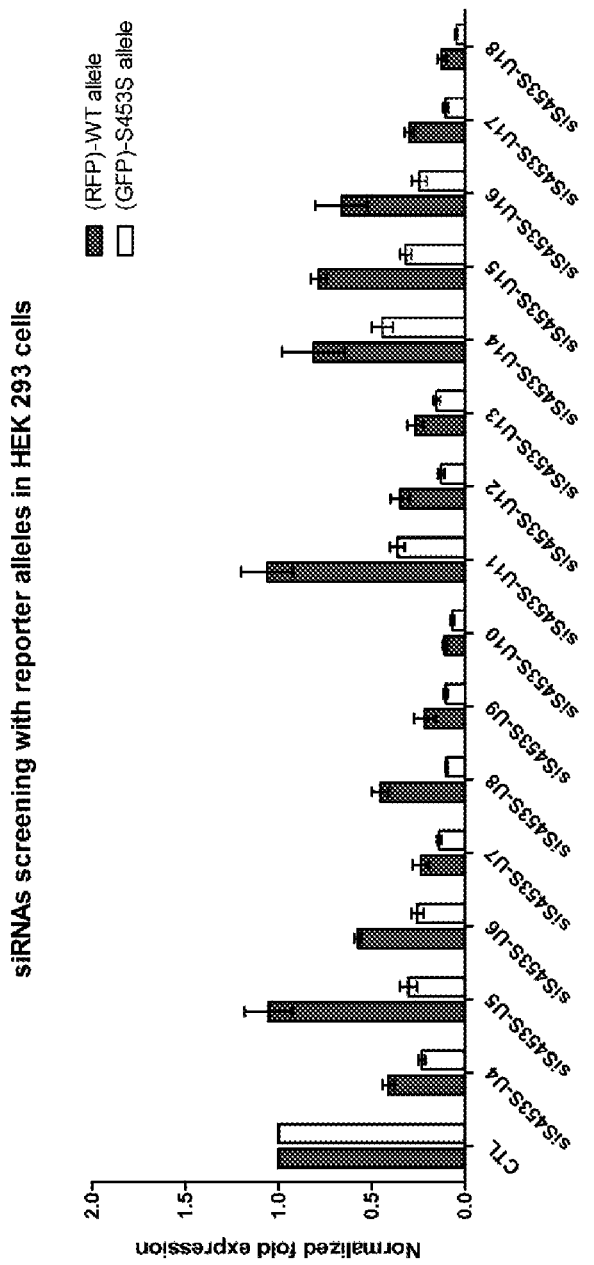
FIG. 14: Assessment of wild type (c.1359C) (black) and S453S SNP (c.1359T) containing allele (white) expression by RealTime PCR in Hek293 cells transiently transfected with hRYR2 reporter alleles and siRNA duplexes.

Of interest, several siRNAs targeted to rs3765097 in exon 15 of human RYR2 gene are able to suppress expression of the polymorphism carrier allele leaving minimally altered the expression of the non-carrier one (see FIG. 14).

Materials and Methods
Animal Use

Animals were maintained and bred at the Charles River Laboratories in Calco, Italy, and transferred to the Maugeri Foundation for characterization of the phenotype. Animals were maintained and studied according to the protocols approved by the Animal Care and Use facility at the Maugeri Foundation. The adeno-associated virus delivery was via intra-caudal vein and/or intraperitoneal injection of 100-200 µl of purified virus in adult mice (8 weeks old) and/or neonatal mice (before the 9$^{th}$ day after birth, P9) with a 25 gauge syringe.

Quantitative Real-Time PCR

Real-time PCR was performed using the Bio-Rad CFX96 Real-Time PCR Detection System and analyzed using the Bio-Rad CFX Manager software package (Bio-Rad Laboratories, Inc., USA). Briefly, total RNA was purified with Rneasy mini kit (Qiagen) from Hek293 cells transiently transfected with reporter alleles and siRNA duplexes or with reporter alleles and pAAV2.1-miRyRU10 or pAAV2.1-miRNAscramble. Absorbance at 260 nm (A260) was measured for each RNA sample using the NanoDrop (ND-1000) spectrophotometer (NanoDrop Technologies, Wilmington, Del., USA). A total amount of 1 µg template RNA was used for retrotranscription performed with iScript cDNA Synthesis kit (Bio-Rad Laboratories, Inc., USA). Quantitative real-time PCR analysis was performed in optical 96-well plates using CFX96 detection module (Bio-Rad Laboratories, Inc.) in triplicate with SsoFast EvaGreen Supermix using specific primer mix to selectively amplify GFP or RFP sequence (Forward: 5'-CTATATCATGGCCGACAAGCAG-3' (SEQ ID NO:120), 5'-GCGTGATGAACTTCGAGGACG-3' (SEQ ID NO:121) Reverse: 5'-GCTCGTCCATGCCGAGCGTG-3' (SEQ ID NO:122), 5'-CAGCCCATGGTCTTCTTCTGC (SEQ ID NO:123), FLAG or HA (Forward: 5'-GAACCTCCAGCGATACTGC-3' (SEQ ID NO:124), Reverse: 5'-CTGGTACCCTTGTCATCGTCATCCTTGTAATCG-3' (SEQ ID NO:125), 5'-CTGGTAACCTATTAAGCGTAGTCAGGTAC (SEQ ID NO:126), to quantify mutated allele or wild type mRNA respectively, and 20 ng of cDNA template. Values for threshold cycle (Ct) determination were generated automatically by the Bio-Rad CFX Manager software 1.5. GAPDH was used as internal reference using the following primers: Forward: 5'-AAATCCCATCACCATCTTCC-3' (SEQ ID NO:127) and Reverse: 5'-GGTTCACACCCATGACGAAC-3' (SEQ ID NO:128).

Florescence Microscopy

Hek293 cells transiently transfected with reporter alleles and siRNA duplexes were fixed on coverslips in 3.7% paraformaldehyde for 10 minutes at room temperature. Coverslips were then washed in PBS with gentle shaking. The cells were washed several times in PBS and mounted on slides with mounting medium (Dako Fluorescent Mounting Medium, Dako North America, Inc, CA). Confocal microscopy was performed with a Leica TCS-SP2 digital scanning confocal microscope equipped with a HCX PL APO 40x/numerical aperture=1.25 oil immersion objective. We used the 488-nm Argon laser line for excitation of EmGFP and 594 nm He/Ne laser line for excitation of RFP. The pinhole diameter was kept at Airy 1. Images were exported to Adobe Photoshop CS3 (Adobe Systems, Mountain View, Calif.).

Immunoblotting

Hek293 cells transiently transfected with reporter alleles and siRNA duplexes or with reporter alleles and pAAV2.1-miRyRU10 or pAAV2.1-miRNAscramble have been lysated in RIPA buffer and total proteins extracted. Total proteins (30 µg/sample, quantified by the BCA assay) were resolved by SDS-gel electrophoresis, Mini PROTEAN TGX Stain-Free 4-15% gradient Gels (BIORAD) using 10× Tris/Glycine/SDS buffer (BIORAD), and blotted on 0.2 µm nitrocellulose using Trans Blot Turbo Transfer System (BIORAD). The membranes were probed with different antibodies: anti-FLAG (F3165, SIGMA), anti-HA (H3663, SIGMA) and anti-Actin (A1978, SIGMA) as reference protein. Secondary antibodies were conjugated with HRP (1:5000, Promega). Specific signals were developed using the Clarity Western ECL substrate (BIORAD) and detected using ChemiDoc MP Imaging System (BIORAD).

ECG Monitoring and Drug Testing

ECG radiotelemetry monitors (Data Sciences International) were implanted subcutaneously under general anaesthesia (Avertin 0.025 mg/kg). Body temperature was maintained at 37° C. by use of a thermally controlled heating pad (Harvard Apparatus). After 72 hours of recovery from surgery, phenotype characterization was performed. First, basal ECG was recorded for 10 minutes looking for the presence of arrhythmias. Subsequently, mice were injected with epinephrine and caffeine (2 and 120 mg/kg, respectively, by I.P.) to induce ventricular arrhythmias under a controlled stimulus. All animal were freely moving while ECG recordings were performed.

Isolation of Adult Mice Ventricular Myocytes

Ventricular myocytes were isolated using an established enzymatic digestion protocol (Hilal-Dandan et al., 2000) from $RyR2^{R4496C/+}$ heterozygous mice, $RyR2^{R4496C/+}$ heterozygous mice infected with AAV9-miRyR2-U10 and wild-type (WT) mice (8 weeks) of either sex.

Electrophysiological Recordings in Isolated Ventricular Myocytes

Cardiomyocytes were seeded on a glass bottom perfusion chamber mounted on the stage of an inverted microscope. After 5 minutes, the myocytes were bathed with the solution containing (in mmol/L): 140 NaCl, 4 KCl, 2 $CaCl_2$, 1 $MgCl_2$, 10 HEPES, and 5 glucose, pH 7.4, with NaOH. A thermostatically controlled heating ring surrounding the dish was used to maintain the bath solution at 35° C. Transmembrane potentials were recorded in whole cell current clamp mode using a MultiClamp 700B amplifier (Axon Instruments). Patch electrodes were pulled from borosilicate glass (WPI, Inc.) on a P-97 horizontal puller (Sutter Instruments). The electrodes had a resistance of 2 to 3 MΩ when filled with patch electrode solutions containing (in mmol/L): 120 potassium aspartate, 20 KCl, 1 $MgCl_2$, 4 $Na_2ATP$, 0.1 GTP, 10 HEPES, 10 glucose, pH 7.2, with NaOH. All signals were acquired at 10 kHz (Digidata 1322A, Axon Instruments) and analyzed with the use of personal computer running pCLAMP version 9.2 software (Axon Instruments). Only quiescent, calcium-tolerant, rod-shaped cells with clear cross striations and a resting potential of less than or equal to −80 mV were used for electrophysiological recordings. Myocytes were electrically stimulated by intracellular current injection through patch electrodes using depolarizing pulses with duration of 3 ms and amplitude of 1.5 times the minimal current needed to evoke and action potential. The liquid junction potential between pipette and bath solution was calculated with pCLAMP software and corrected after experiments.

Vector Design and Production

The siRYR2-U10 siRNA duplex sequence, designed to target RYR2 mRNA (NM_023868.2) containing the R4496C mutation, was cloned into an artificial miRNA expression vector, BLOCK-iT™ Pol II miR RNAi Expression vector (Life Technologies, Cat. No: K4936-00), that allows continuous and long term expression of the silencing molecule. The cloning procedure was based on ligation of annealed oligonucleotides (5'TGCTGTAAAAGTTGCAAGCAAAATAGTTTTG 3' (SEQ ID NO:129), 5'GCCACTGACTGACTAT-TTTGCGCAACTTTTAC 3' (SEQ ID NO:130), 5'CCTGGTAAAAGTTGCGCAAAATAGTCAGTCA 3' (SEQ ID NO:131), 5'GTGGCCAAAACTAT-TTTGCTTGCAACTTTTAC 3' (SEQ ID NO:132) with the linearized vector (pcDNA™6.2-GW/EmGFPmiR-(Life Technologies, Cat. No: K4936-00)).

From the obtained plasmid, a fragment consisting in CMV promoter, EmGFP, premiRNA sequence and TKpolyA was amplified by PCR with specific primers (Forward: 5' TAGCTAGCTGCTTCGCGATGTACGG 3' (SEQ ID NO:133) and Reverse 5' GTGAAT-TCGAACAAACGACCCAACACCCG 3' (SEQ ID NO:134) including the NheI (Forward) and Eco RI (Reverse) cloning site and inserted into the pre-digested Nhe I-Eco RI sites adeno associated viral backbone vector pAAV-2.1 provided by the Adeno-Associated Virus (AAV) vector Core facility (Tigem, Napoli, Italy). All the used plasmids were sequenced.

The AAV production was done in collaboration with the Tigem core facility (http://www.tigem.it/core-facilities/adeno-associated-virus-aav-vector-core). The AAV vectors were produced using a transient transfection of 3 plasmids in 293 cells: pAd helper, pAAV rep-cap (packaging), pAAV Cis (including our insert, miRYR2, cloned in the pAAV2.1-CMV-eGFP plasmid MCS). The vectors were purified by CsCl centrifugation and undergo quality control such as Real Time PCR and Dot Blot analysis for physical titer, or Comassie staining of SDS PAGE to evaluate the presence and purity of capsid proteins, the infectivity (eGFP$^+$ cells/ml, only for CMV-eGFP preps) and the sterility (for preps to be used in large animals). The service returned with a viral preparation in PBS with a total yield $>1\times10^{12}$ genome copies. All AAV stocks were frozen at −80° C. in single vial and thawed during the surgical procedure.

Electron Microscopy

Hearts isolated from WT, heterozygous $RyR2^{R4496C/+}$ and infected heterozygous $RyR2^{R4496C/+}$ mice, were fixed by retrograde aortic perfusion with 3.5% glutaraldehyde in 0.1 mol/L NaCaCo buffer (pH 7.2) and analyzed. Small bundles of papillary muscles were post-fixed in 2% $OsO_4$ in NaCaCo buffer for 2 hours and then block-stained in saturated uranyl acetate. After dehydration, specimens were embedded in an epoxy resin (Epon 812). Ultrathin sections were cut in a Leica Ultracut R microtome (Leica Microsystem, Austria) using a Diatome diamond knife (Diatome Ltd. CH-2501 Biel, Switzerland) and double stained with uranyl acetate and lead citrate. All sections were examined with an FP 505 Morgagni Series 268D electron microscope (FEI Company, Brno, Czech Republic), equipped with Megaview III digital camera and Soft Imaging System (Munster, Germany). The percentage of cardiac cells exhibiting severe structural alterations was quantified. Cells considered severely damaged are characterized by severe structural abnormalities affecting mitochondria in the majority of the interior. In most cases cardiac cells with severely altered mitochondria also present large area of apparently empty cytoplasmic spaces and alterations affecting contractile elements.

Abbreviations

The following abbreviations have been used in the present specification: CASQ2, calsequestrin 2; CPVT, Catecholaminergic Polymorphic Ventricular Tachycardia; CICR, Calcium Induced Calcium Release; CRU, calcium release unit; DAD, Delayed afterdepolarization; EC coupling, excitation-contraction coupling; ECG, electrocardiogram; CMV, Citomegalovirus; GFP, green fluorescent protein; RFP, red fluorescent protein; AAV, Adeno Associated Virus; EP, electrophysiology; I.P., intraperitoneal; ISO, isoproterenol; RYR2, ryanodine receptor type 2; WT, Wild type; siRNA, small interfering RNA; miRNA, microRNA; SNP, Single Nucleotide Polimorphisms; HA, Human influenza hemagglutinin; MRS, Mutant Recognition Site; RNAi, RNA interference; TK polyA, HSV thymidine kinase (TK) polyadenylation signal sequence.

REFERENCES

1. Priori S G, Napolitano C, Colombo B, Memmi M, Bloise R. Mutations of the cardiac Ryanodine receptor (RYR2) gene are associated to heterogeneous clinical phenotypes and high lethality. *Circulation* 2001; 104 (suppl II):335.
2. Lahat H, Pras E, Olender T, Avidan N, Ben Asher E, Man O, Levy-Nissenbaum E, Khoury A, Lorber A, Goldman B, Lancet D, Eldar M. A missense mutation in a highly conserved region of CASQ2 is associated with autosomal recessive catecholamine-induced polymorphic ventricular tachycardia in Bedouin families from Israel. *Am J Hum. Genet.* 2001; 69:1378-1384.
3. Bers, D. M. Cardiac excitation-contraction coupling. *Nature* 415, 198-205 (2002).
4. Franzini-Armstrong, C., Protasi, F. & Tijskens, P. The assembly of calcium release units in cardiac muscle. *Ann. NY Acad. Sci.* 1047, 76-85 (2005).
5. Pieske, B., Maier, L. S., Bers, D. M. & Hassenfuss, G. $Ca^{2+}$ handling and sarcoplasmic reticulum $Ca^{2+}$ content in isolated failing and nonfailing human myocardium. *Circ. Res.* 85, 38-46 (1999).
6. Venetucci L, Denegri M, Napolitano C, Priori S G. Inherited calcium channelopathies in the pathophysiology of arrhythmias. *Nat Rev Cardiol.* 9(10), 561-75 (2012).
7. Liu N, Colombi B, Memmi M, Zissimopoulos S, Rizzi N, Negri S, Imbriani M, Napolitano C, Lai F A, Priori S G. Arrhythmogenesis in Catecholaminergic Polymorphic Ventricular Tachycardia. Insights From a RyR2 R4496C Knock-In Mouse Model. *Circulation Research* 2006; 99:292-298.
8. Cerrone M, Colombi B, Santoro M, Raffale di Barletta M, Scelsi M, Villani L, Napolitano C, Priori S G. Bidirectional Ventricular Tachycardia and Fibrillation Elicited in a Knock-In Mouse Model Carrier of a Mutation in the Cardiac Ryanodine Receptor (RyR2). *Circulation Research* 2005; 96:e77-e82.
9. Denegri M, Bongianino R, Lodola F, Boncompagni S, DeGiusti V C, Avelino-Cruz J E, Liu N, Persampieri S, Curcio A, Esposito F, Pietrangelo L, Marty I, Villani L, Moyaho A, Baiardi P, Auricchio A, Protasi F, Napolitano C, Priori S G. A single delivery of an adeno-associated construct to transfer casq2 gene to knock-in mice affected by catecholaminergic polymorphic ventricular tachycardia is able to cure the disease from birth to advanced age Circulation. 2014; 129(25):267381
10. Elbashir S M, Harborth J, Lendeckel W, Yalcin A, Weber K, Tuschl T. Duplexes of 21-nucleotide RNAs mediate RNA interference in cultured mammalian cells. Nature. 2001 May 24; 411(6836):494-8
11. Hilal-Dandan, R., Kanter, J. R. & Brunton, L. L. Characterization of G-protein signaling in ventricular myocytes from the adult mouse heart: differences from the rat. J. Mol. Cell. Cardiol. 32, 1211-1221 (2000).

The invention claimed is:

1. A double-stranded short interfering nucleic acid (siNA) molecule that inhibits expression of a mutant allele of the cardiac ryanodine receptor type 2 (RYR2) gene, comprising a sense strand and an antisense strand, wherein the sense strand is complementary to the antisense strand, and wherein the sense strand comprises a nucleotide sequence selected from the group consisting of SEQ ID NOs: 4 through 18; SEQ ID NOs: 21 through 35; SEQ ID NOs: 38 through 52; SEQ ID NOs: 55 through 69; SEQ ID NOs: 72 through 86; SEQ ID NOs: 89 through 104; and SEQ ID NOs: 107 through 119.

2. The siNA molecule according to claim 1, which is a short interfering RNA (siRNA), a double-stranded RNA (dsRNA), a short hairpin RNA (shRNA), or a circular RNA molecule.

3. The siNA molecule according to claim 1, wherein:
a) the antisense strand comprises a sequence that is complementary to at least a part of an RNA associated with the expression of the mutant allele;
b) at least some of the nucleotides comprise modifications; and/or
c) in the siNA, at least one phosphothioate linkage is present.

4. The siNA molecule according to claim 1, wherein the sense strand comprises (SEQ ID NO: 112)
5'-UAUUUUGCUUGCAACUUUUAC-3'.

5. The siNA molecule according to claim 3, wherein the modifications comprise 2'0-methyl modifications.

6. The siNA molecule according to claim 5, wherein the modifications comprise a 2'fluoro modification.

7. A composition comprising a recombinant plasmid or viral vector, which expresses the siNA molecule according to claim 1 when delivered to target cells or tissues.

8. The composition according to claim 7, wherein the viral vector is a serotype 9 adeno-associated viral (AAV2/9) vector, a serotype 6 adeno-associated viral (AAV2/6) vector, or a serotype 8 adeno-associated viral (AAV2/8) vector.

9. The composition according to claim 7, further comprising a pharmaceutical carrier or diluent.

10. The composition according to claim 9, wherein the pharmaceutical carrier or diluent is selected from a cationic lipid and a liposome.

11. A method of therapeutically or prophylactically treating a subject suffering from a condition associated with a mutation in the cardiac RYR2 gene, or preventing or reverting structural abnormalities of the calcium release units (CRUs) and in the mitochondria of a subject, the method comprising administering to the subject the SiNA molecule according to claim 1, wherein
a) the siNA molecule targets the RNA associated with the expression of the mutant allele of the RYR2 gene of the subject;
b) the siNA molecule targets the RNA associated with the expression of a single nucleotide polymorphism (SNP) in the coding region of the RYR2 gene, and said SNP co-segregates with the mutation in the same allele or in the opposite, whereby the RYR2 allele that carries the mutation is silenced; and/or
c) the abnormalities are associated with the R4496C mutation in the RYR2 gene.

12. The method according to claim 11, wherein:
a) the siNA is expressed from a viral vector delivered to the subject; and/or
b) the condition is a cardiac disease.

13. The method according to claim 12, wherein the viral vector is a serotype 9 adeno-associated viral (AAV2/9) vector, a serotype 6 adeno-associated viral (AAV2/6) vector, or a serotype 8 adeno-associated viral (AAV2/8) vector.

14. The method according to claim 13, wherein the AAV2/9 or AAV2/6 or AAV2/8 is delivered to the subject's cardiac myocytes.

15. The method according to claim 11, wherein the condition is catecholaminergic polymorphic ventricular tachycardia (CPVT), arrhythmogenic right ventricular cardiomyopathy (ARVC), idiopathic ventricular fibrillation (IVF) and Hypertrophic cardiomyopathy, or dilated cardiomyopathy due to RYR2 gene mutations.

16. A kit comprising the siNA of claim 1.

* * * * *

SEQUENCE LISTING

```
<160> NUMBER OF SEQ ID NOS: 134

<210> SEQ ID NO 1
<211> LENGTH: 14904
<212> TYPE: DNA
<213> ORGANISM: Homo sapiens

<400> SEQUENCE: 1
atggccgatg ggggcgaggg cgaagacgag atccagttcc tgcgaactga tgatgaagtg      60
gttctgcagt gcaccgcaac catccacaaa gaacaacaga agctatgctt ggcagcagaa     120
ggatttggca acagactttg tttcttggag tccacttcca attccaagaa tgtgccccca     180
gacctctcca tctgcacctt tgtgctggag cagtccctct ctgtccgggc gctgcaggag     240
atgctggcta acaccgtgga gaaatcagaa gggcaagttg atgtggaaaa atggaaattc     300
atgatgaaga ctgctcaagg tggtggtcat cgaacactcc tctacggaca tgccatattg     360
ctgcgccatt cctatagtgg catgtatctg tgctgcctgt ccacctcccg gtcttcaact     420
gataagctgg cttttgatgt tggcttgcaa gaggacacca caggggaggc ttgttggtgg     480
accatacacc ctgcctctaa gcagcgatca gaaggagaaa aagtacgagt tggagatgac     540
ctcatcttag ttagcgtgtc ctctgaaagg tacttgcact tgtcttatgg caacggcagc     600
ttacacgtgg atgccgcttt ccagcagact ctctggagcg tggccccaat cagctcagga     660
agtgaggcag cccaagggta tctcattggt ggtgatgtcc tcaggttgct gcatggacac     720
atggacgagt gtctcactgt cccttcagga gaacatggtg aagagcagcg gagaactgtt     780
cattatgaag gtggcgctgt gtctgttcat gcacgttccc tttggagact agagacgcta     840
```

```
agagttgcgt ggagtggaag ccacataaga tggggacagc cattccgact acgccatgtc    900
acaacaggaa aatacttgag tctcatggaa gacaaaaacc ttctactcat ggacaaagag    960
aaagctgatg taaaatcaac agcatttacc ttccggtctt ccaaggaaaa attggatgta   1020
ggggtgagaa aagaagtaga tggcatggga acatctgaaa taaaatacgg tgactcagta   1080
tgctatatac aacatgtaga cacaggccta tggcttactt accagtctgt ggacgtgaaa   1140
tccgtgagaa tgggatctat acaacgtaag gctattatgc atcatgaagg ccacatggat   1200
gatggcataa gtttgtcgag atcccagcat gaagaatcac gcacagcccg agttatccgg   1260
agcacagtct tccttttcaa tagatttata aggggccttg atgctctcag caagaaagcg   1320
aaggcttcca cagtcgattt gcctatagag tccgtaagcc taagtctgca ggatctcatt   1380
ggctacttcc accccccaga tgagcattta gagcatgaag acaaacagaa cagactacga   1440
gccctgaaga atcggcaaaa tctcttccag gaagagggaa tgatcaacct cgtgcttgag   1500
tgcatagacc gtttgcacgt ctacagcagt gcagcacact ttgctgatgt tgctgggcga   1560
gaagcaggag agtcttggaa atccattctg aattctctgt atgagttgct ggcggctcta   1620
attagaggaa atcgtaaaaa ctgtgctcaa ttttctggct ccctcgactg gttgatcagc   1680
agattggaaa gactggaagc ttcttcaggc attctggaag ttttacactg tgttttagta   1740
gaaagtccag aagctctaaa tattattaaa gaaggacata ttaaatctat tatctcactt   1800
ttagacaaac atgaagaaa tcacaaggtt ctggatgtct tgtgctcact ctgtgtttgc   1860
cacggggttg cagtccgttc taaccagcat ctcatctgtg acaatctcct accaggaaga   1920
gacttgttat tgcagacacg tcttgtgaac catgtcagca gcatgagacc caatattttt   1980
ctgggcgtca gtgaaggttc tgctcagtat aagaaatggt actatgaatt gatggtggac   2040
cacacagagc cctttgtgac agctgaagca actcacctgc gagtgggctg gcttccact    2100 gaaggatatt ctccctaccc tggagggggc gaagagtggg gtggaaatgg tgttggagat   2160
gatctcttct cctatggatt tgatggcctt catctctggt caggttgtat tgctcgtact   2220
gtaagctcac caaaccaaca tctgttaaga actgatgatg tcatcagttg ctgtttagat   2280
ctgagtgccc caagcatctc gttccgaatt aatggacaac tgttcaagg aatgtttgag   2340 aatttcaaca tcgatggcct cttcttttca gtcgttagtt tctctgcagg aataaaagta   2400
cgctttctgc ttggagggcg acatggagaa ttcaaatttc ttcctccacc tgggtatgct   2460
ccttgttatg aagctgttct gccaaaagaa aagttgaaag tggaacacag ccgagagtac   2520
aagcaagaaa gaacttacac acgcgacctg ctgggcccca cagtttccct gacgcaagct   2580
gccttcacac ccatccctgt ggataccagc cagatcgtgt tgcctcctca tctagaaaga   2640
ataagagaaa aactggcaga gaatatccat gaactctggg ttatgaataa aattgagctt   2700
ggctggcagt atggtccggt tagagatgac aacaagagac aacacccatg cctggtggag   2760
ttctccaagc tgcctgaaca ggagcgcaat tacaacttac aaatgtcgct tgagaccctg   2820
aagactttgt tggcattagg atgtcatgtg ggtatatcag atgaacatgc tgaagacaag   2880
gtgaaaaaaa tgaagctacc caagaattac cagctgacaa gtggatacaa gcctgcccct   2940
atggacctga gctttatcaa actcaccca tcacaagaag caatggtgga caagttggca   3000
gaaaatgcac ataatgtgtg ggcgcgggat cgaatccggc agggctggac ttatggcatc   3060
caacaggacg taagaacag aagaaatcct cgccttgttc cctacactct tctggatgac   3120
cgaaccaaga aatccaacaa ggacagcctc cgcgaggctg tgcgcacgct gctggggtac   3180
ggctacaact tggaagcacc agatcaagat catgcagcca gagccgaagt gtgcagcggc   3240
```

-continued

```
accggggaaa ggttccgaat cttccgtgcc gagaagacct atgcagtgaa ggccggacgg    3300
tggtattttg aatttgagac ggtcactgct ggagacatga gggttggttg gagtcgtcct    3360
ggttgtcaac cggatcagga gcttggctca gatgaacgtg cctttgcctt tgatggcttc    3420
aaggcccagc ggtggcatca gggcaatgaa cactatgggc gctcttggca agcaggcgat    3480
gtcgtggggt gtatggttga catgaacgaa cacaccatga tgttcacact gaatggtgaa    3540
atccttcttg atgattcagg ctcagaactg gctttcaagg actttgatgt tggcgatgga    3600
ttcatacctg tgtgtagcct tggagtggct caagtgggta ggatgaactt tggaaaggat    3660
gtcagcacct tgaaatattt caccatctgt ggcttacaag agggctatga accatttgcc    3720
gttaatacaa acagggatat taccatgtgg ctgagcaaga ggcttcctca gtttcttcaa    3780
gttccatcaa accatgaaca tatagaggtg accagaatag acggcaccat agacagttcc    3840
ccatgtttaa aggtcactca gaagtctttt ggttctcaga cagcaacac tgatatcatg    3900 ttttatcgcc tgagcatgcc gatcgagtgc gcggaggtct tctccaagac ggtggctgga    3960
gggctccctg gggctggcct ttttgggccc aagaatgact tggaagatta tgatgctgat    4020
tctgactttg aggttctgat gaagacagct catggccatc tagtgcccga tcgtgttgac    4080
aaagacaaag aagctactaa accagagttt aacaaccaca agattatgc ccaggaaaag    4140 ccctctcgtc tgaaacaaag attttttgct agaagaacaa agccagatta cagcacaagc    4200
cattctgcaa gactcaccga gatgtccctt gctgatgatc gggatgacta tgatttcttg    4260
atgcaaacgt ccacgtacta ttactcagtg agaatctttc ctggacaaga acctgctaat    4320
gtctgggtgg gctggattac atcagatttc catcagtatg acacaggctt tgacttggac    4380
agagttcgca cagtaacagt tactctagga gatgaaaaag gaaagtgca tgaaagcatc    4440 aaacgcagca actgctatat ggtatgtgcg ggtgagagca tgagccccgg gcaaggacgc    4500
aacaataatg gactggagat tggctgtgtg gtggatgctg ccagcgggct gctcacattc    4560
attgccaatg gcaaggaact gagcacatac tatcaggtgg aaccgagtac aaaattattt    4620
cctgcggttt ttgcacaagc tacaagtccc aatgttttcc agtttgagtt gggaagaata    4680
aagaatgtga tgcctctctc ggcgggatta ttcaagagtg agcacaagaa ccccgtgccg    4740
cagtgccccc cgcgcctcca cgtgcagttc ctgtcacacg tcctgtggag cagaatgccc    4800
aaccagtttt tgaaggtaga tgtgtctcga ataagtgaac gccaaggctg gttggtgcag    4860
tgtttggatc ctctgcagtt catgtctctt catatccctg aggaaaacag atctgttgac    4920
atcttagagt tgacagagca ggaggaattg ctgaaatttc actatcacac tctccggctc    4980
tactcagccg tctgtgctct tgggaaccac cgggtggccc atgccctgtg cagccatgtg    5040
gatgaacctc agctcctcta tgccattgag aacaagtaca tgcctggttt gctgcgtgct    5100
ggctactatg acctgctgat tgacatccac ctgagctcct atgccactgc caggctcatg    5160
atgaacaacg agtacattgt ccccatgacg gaggagacga gagcatcac cctgttccct    5220 gatgagaaca aaaaacacgg ccttccaggg atcggcctca gcacctccct caggccacgg    5280
atgcagtttt cctcccccag ttttgtaagc attagtaatg aatgttacca gtacagtcca    5340
gagttcccac tggacatcct caagtccaaa accatacaga tgctgacaga agctgttaaa    5400
gagggcagtc ttcatgcccg ggacccagtt ggagggacta ctgaattcct ctttgtacct    5460
ctcatcaagc ttttctatac cctgctgatc atgggcatct tcacaacga ggacttgaag    5520 cacatcttgc agttgattga gcccagtgtg tttaagaag ctgccactcc ggaggaggag    5580
```

```
agtgacacgc tggagaaaga gctcagtgtg gacgatgcaa agctgcaagg agctggtgag      5640
gaagaagcca agggggcaa gcggcccaag gaaggcctgc tccaaatgaa actgccagag       5700
ccagttaaat tgcagatgtg cctactgctt cagtacctct gtgactgcca ggtccggcac      5760
cggatagaag ccattgtagc cttttcagat gattttgtgg ctaagctcca agacaatcaa      5820
cgtttccgat acaacgaagt catgcaagcc ttaaacatgt cagctgcact cacagccagg      5880
aagacaaagg aatttagatc accacctcaa gaacagatca atatgcttct caattttaag      5940
gatgacaaaa gtgaatgtcc atgtccagaa gaaattcgtg accaactatt ggatttccat      6000
gaagatttga tgacacattg tggaattgag ctggatgaag atgggtctct ggatggaaac      6060
agtgatttaa caattagagg gcgtctgcta tccctggtag aaaaggtgac atatctgaag      6120
aagaagcaag cagaaaaacc agttgagagt gactccaaaa agtcctccac tctgcagcag      6180
ctgatttctg agaccatggt ccgatgggct caggagtctg tcattgaaga ccccgagctg      6240
gtgagggcca tgtttgtgtt gctccatcgg cagtatgacg gcattggggg tcttgttcgg      6300
gccctgccaa agacctacac gataaatggt gtgtccgtgg aggacaccat caacctgctg      6360
gcatcccttg gtcagattcg gtccctgctg agtgtgagaa tgggcaaaga agaagagaag      6420
ctcatgattc gtggattagg ggatattatg aataacaaag tgttttacca gcaccctaat      6480
ctcatgaggg cactggggat gcacgagact gtgatggagg tcatggtgaa cgtccttgga      6540
ggtggagagt ccaaggaaat cacctttccc aagatggtgg ccaactgttg ccgttttctc      6600
tgttacttct gtcgtataag taggcagaat caaaaagcta tgtttgatca tctcagttat      6660
ttactggaaa acagcagtgt tggtcttgcc tccccagcta tgagaggttc aacaccactg      6720
gatgtggctg cagcttcggt gatggataat aatgaactag cattagctct gcgtgagccg      6780
gatctagaaa aggtagttcg ttatttggct ggttgtggac tgcaaagttg ccagatgctg      6840
gtgtctaagg gctatccaga cattgggtgg aacccagttg aaggagagag atatcttgac      6900
tttcttagat ttgctgtctt ctgtaatggg gagagtgtgg aggaaaatgc aaatgtcgtg      6960
gtgagattgc tcattcggag gcctgagtgt tttggtcctg ctttgagagg agaaggtggg      7020
aatgggcttc ttgcagcaat ggaagaagcc atcaaaatcg ccgaggatcc ttcccgagat      7080
ggtccctcac caaatagcgg atccagtaaa acacttgaca cagaggagga ggaagatgac      7140
actatccaca tggggaacgc gatcatgacc ttctattcag cttttgattga cctcttggga      7200 cgctgtgctc ctgagatgca tttgattcat gccgggaagg gagaagccat cagaattagg      7260
tccattttga gatccctcat tcccctggga gatttggtgg cgttatcag catcgcttt       7320 cagatgccaa caatagccaa agatgggaat gtggtggaac ctgacatgtc tgcggggttt      7380
tgcccagatc acaaggcagc catggttttt ttccttgaca gggtctatgg gattgaggtt      7440
caagacttcc tcctccatct tcttgaggtt ggctttctgc cagatctccg ggcggctgct      7500
tctttagata cggcagcttt gagtgctaca gacatggcct tggccctcaa tcggtacctt      7560
tgcacagccg tcttgccatt gttaacaaga tgtgctcctc tctttgctgg cacagagcac      7620
cacgcttctc tcattgactc attacttcat actgtgtata gactttctaa gggctgttca      7680
cttaccaaag ctcagcggga ttccataaag gtttgtttac tctctatttg tggacaactg      7740
agaccttcta tgatgcagca cttactcaga agattagtat ttgatgttcc attattaaat      7800
gaacacgcaa agatgcctct taaactgctg acaaatcatt atgaaagatg ctggaaatat      7860
tactgcctgc ctggagggtg gggaaacttt ggtgctgcct cagaagaaga acttcattta      7920
tcaagaaagt tgttctgggg catttttgat gccctgtctc aaaagaaata tgaacaagaa      7980
```

```
cttttcaaac tggcactgcc ttgcctgagt gcagttgcgg gagcttttgcc tccagactac    8040 atggagtcaa attatgtcag tatgatggaa aaacagtcat caatggattc tgaagggaac    8100
tttaacccac aacctgttga tacctcaaat attacaattc ctgagaaatt ggaatacttc    8160
attaacaaat atgcagaaca ctcccatgac aaatggtcaa tggacaagtt ggcaaatgga    8220
tggatttatg gagaaatata ttcagactct tctaaggttc agccattaat gaagccatat    8280
aagctattgt ctgaaaagga aaagaaatt tatcgctggc caatcaaaga atctttaaaa     8340
actatgctgg cttggggctg gagaattgaa agaactcggg agggagacag catggccctt    8400
tacaaccgga ctcgtcgtat ttctcagaca agccaggttt ctgtggacgc tgcccatggt    8460
tacagtcccc gggccattga catgagcaat gttacactat ctagagacct gcatgctatg    8520
gcagaaatga tggctgaaaa ctaccataat atatgggcaa agaaaaagaa atggagttg     8580 gagtccaaag gaggaggaaa ccatcctctg ctggtgccct atgatacact gacagccaaa    8640
gagaaagcca aggatagaga aaaagcacag gacatcctca gttcttgca gatcaatgga    8700 tatgctgtat ccagaggatt taaggacctg gaactggaca cgccttctat tgagaaacga    8760
tttgcctata gtttcctcca acaactcatt cgctatgtgg atgaagccca tcagtatatc    8820
ctggagtttg atggtggcag cagaggcaaa ggagaacatt tcccttatga acaagaaatc    8880
aagttctttg caaagtcgt tcttcctta attgatcagt atttcaaaaa ccatcgttta      8940
tacttcttat ctgcagcaag cagacctctc tgctctggag acatgcttc caacaaagag     9000 aaagaaatgg tgactagcct attctgcaaa cttggagttc ttgtcaggca taggatttca    9060
ctatttggca atgatgcaac atcaattgtc aactgtcttc atatttggg tcagactttg     9120 gatgcaagga cagtgatgaa gactggcctg gagagtgtta aaagtgcact cagagctttt    9180
ctggacaacg ctgcagagga tctggagaag accatggaaa acctcaagca gggccagttc    9240
actcacaccc gaaaccagcc caaaggggtt actcagatta tcaattacac cacagtggcc    9300
ctgctgccaa tgctgtcttc attatttgaa catattggcc agcatcagtt cggagaagac    9360
ctaatattgg aagatgtcca ggtgtcttgt tatagaattc tgactagctt atatgctttg    9420
ggaaccagca agagtattta cgtggagagg caacgttctg cattaggaga atgtctagct    9480
gcctttgctg gtgcttttcc tgtagcattt ttggaaactc atctggacaa acataatatt    9540
tactccatct acaataccaa gtcttcacga gaaagagcag ctctcagttt gccaactaat    9600
gtggaagatg tttgtccaaa cataccgtct ttggagaaac tcatggaaga atcgtggaa     9660 ttagccgagt ccggcattcg ctacactcaa atgccacatg tcatggaagt catactgccc    9720
atgctttgca gctacatgtc tcgttggtgg gagcatggac ctgagaacaa tccagaacgg    9780
gccgagatgt gctgcacagc cctgaactca gagcacatga acacacttct agggaacata    9840
ttgaaaatca tataataa cttggggatt gatgagggag cctggatgaa gaggctagca      9900 gtgtttccc agcctataat aaataaagtg aaacctcagc tcttgaaaac tcatttcttg     9960
ccgttaatgg agaaactcaa gaaaaaggca gctacggtgg tgtctgagga agaccacctg   10020
aaagctgagg ccaggggga catgtcggag gcagaactcc tcatcctaga tgagttcacc    10080
acactggcca gagatctcta tgccttctac cctctcttga ttagatttgt ggactataac   10140
agggcaaagt ggctaaagga gcctaaccca gaagcagagg agctcttccg catggtggct   10200
gaagtgttta tctactggtc gaagtcccat aatttcaaaa gagaagagca gaacttcgtt   10260
gtacagaatg aaatcaacaa tatgtctttc cttattactg ataccaagtc aaagatgtca   10320
```

```
aaggcagctg tttctgatca ggaaaggaag aaaatgaagc gcaaaggaga tcggtattcc   10380
atgcagacct ctctgattgt agcagctctg aagcggttac tgcccattgg gttgaacatc   10440
tgtgcccctg gggaccagga gctcattgct ctggccaaaa atcgatttag cctgaaagat   10500
accgaggatg aagtacgaga tataatccgc agcaatattc atttacaagg caagttggag   10560
gatcctgcta ttagatggca aatggctctt tacaaagact taccaaacag gactgatgat   10620
acctcagatc cagagaagac ggtagaaaga gtattggata tagcaaatgt gcttttttcat   10680 cttgaacaga agtctaaacg tgtgggtcgg agacattact gtctggtgga acatcctcag   10740
agatctaaaa aggctgtatg gcataaacta ctgtccaagc agaggaaaag ggctgttgta   10800
gcctgcttcc ggatggcccc cttatataat ctgccaaggc atcgggctgt caatctcttt   10860
cttcagggat atgaaaagtc ttggattgaa acagaagaac attactttga agataaactg   10920
atagaagatt tagcaaaacc tggggctgaa cctccagaag aagatgaagg cactaagaga   10980
gttgatcctc tacatcagct gatccttctg tttagtcgga cagctttaac agagaaatgc   11040
aaactggagg aagatttttt atatatggcc tatgcagata ttatggcaaa gagttgtcat   11100
gatgaggaag atgacgatgg tgaagaggaa gtgaagagtt ttgaagaaaa agaaatggaa   11160
aagcaaaagc ttctatacca gcaagcccga ctccacgatc gtggcgcggc tgagatggtg   11220
ctacagacaa tcagtgccag caaaggtgaa actggaccaa tggtagcagc tactctgaaa   11280 cttgaattg ctatttttaaa tggtgggaac tccacagtac agcagaaaat gcttgactac   11340
ctcaaggaga aaaaggatgt gggcttcttt cagagcctgg ccggcctgat gcagtcatgt   11400
agtgtccttg acctaaatgc atttgagcga caaaacaaag ctgaaggtct tgggatggtg   11460
acagaggaag gatcaggaga aaaggttctg caggacgatg agttcacctg tgacctcttc   11520
cgattcctgc aactactctg tgagggacac aactcagatt ttcagaatta tctgagaact   11580
cagactggca ataatacaac tgtcaacata attatctcca ctgtagacta cctactgaga   11640
gttcaggaat caattagtga cttttattgg tattactctg ggaaagatgt tattgatgaa   11700
caaggacaac ggaatttctc caaagctatc caagtggcaa acaagtctct taacactctt   11760
acagagtata ttcagggtcc ttgcactggg aatcaacaga gtttggcaca cagcaggctg   11820
tgggatgctg tggtcggctt tcttcatgtg tttgcccata tgcagatgaa gctgtcgcag   11880
gattccagtc aaattgagct attaaaagaa ttaatggatc tgcagaagga tatggtggtc   11940
atgttgctgt ccatgttaga aggtaatgtt gttaatggaa cgattggcaa acagatggtg   12000
gatatgcttg tggaatcttc caacaacgtg gagatgattc tcaaattttt tgacatgttc   12060
ttaaaactaa aggatttgac gtcgtctgat acttttaaag aatatgaccc cgatggcaag   12120
ggagtcattt ccaagaggga cttccacaaa gcgatggaga gccataagca ctacacgcag   12180
tcagaaacgg aatttctttt gtcttgtgcg agacggatg agaatgaaac cctcgactac   12240
gaagagttcg tcaaacgctt ccacgaacct gcgaaggaca tcggcttcaa cgtcgccgtc   12300
cttctgacaa acctctctga gcacatgccc aacgatacccc gacttcagac ttttctggaa   12360
ttagcagaga gcgtcctgaa ttatttccag ccctttctgg gccgcatcga aatcatggga   12420
agcgccaaac gcatcgagag ggtctatttt gaaatcagtg agtccagccg aacccagtgg   12480
gagaagcccc aggtcaagga gtccaaaaga cagttcatat ttgacgtggt caacgaaggc   12540
ggagagaaag agaagatgga actctttgtg aacttctgcg aggacaccat ctttgaaatg   12600
cagctggcgg ctcagatctc ggagtcggac ttgaacgaga ggtcagcgaa taaggaagaa   12660
agcgagaagg agaggccgga agagcagggg ccgaggatgg ctttcttctc cattctgacg   12720
```

-continued

```
gtcaggtcgg ccctgtttgc gctcaggtac aatatcttga cccttatgcg aatgctcagt    12780
ctgaagagcc tgaagaagca gatgaaaaaa gtaaaaaaga tgaccgtgaa ggacatggtc    12840
acggccttct tttcatccta ctggagtatt ttcatgaccc tcttgcactt cgtggccagc    12900
gttttcagag gcttttttccg catcatttgc agcctgctgc ttgggggaag cctcgtcgaa    12960
ggtgctaaaa agatcaaagt tgcagaactg ttagccaaca tgccagaccc cactcaggat    13020
gaggttagag gagatgggga ggagggagag aggaaacccc tggaagccgc cctgccctcc    13080
gaggatctga ccgacttaaa ggagctgaca gaggaaagtg accttctttc ggacatcttt    13140
ggcctggatc tgaagagaga aggaggacag tacaaactga ttcctcataa tccaaatgct    13200
gggctcagtg acctcatgag caacccagtc cccatgcctg aggtgcagga aaaatttcag    13260
gaacagaagg caaagaaga agaaaaggaa gaaaagaag aaaccaaatc tgaacctgaa    13320
aaagccgagg gagaagatgg agaaaaagaa gagaaagcca aggaagacaa gggcaaacaa    13380
aagttgaggc agcttcacac acacagatac ggagaaccag aagtgccaga gtcagcattc    13440
tggaagaaaa tcatagcata tcaacagaaa cttctaaact attttgctcg caacttttac    13500
aacatgagaa tgttagcctt atttgtcgca tttgctatca atttcatctt gctctttat    13560 aaggtctcca cttcttctgt ggttgaagga aaggagctcc ccacgagaag ttcaagtgaa    13620
aatgccaaag tgacaagcct ggacagcagc tcccatagaa tcatcgcagt tcactatgta    13680
ctagaggaga gcagcggcta catggagccc acgttgcgta tcttagctat tctgcacacg    13740
gtcatttctt tcttctgcat cattggatac tactgcttga aagtcccatt ggttattttt    13800
aagcgagaaa aggaagtggc acggaaattg gaatttgatg ggctttatat tacagaacag    13860
ccttcagaag atgatattaa aggccagtgg gatagactcg taatcaacac acagtcattt    13920
cccaacaact actgggacaa atttgttaaa agaaaggtta tggataaata tggagagttc    13980
tacggccgag acagaatcag tgaattactt ggcatggaca aggcagctct ggacttcagt    14040
gatgccagag aaaagaagaa gccaaagaaa gacagctcct tatcagctgt actgaactcc    14100
attgatgtga agtatcagat gtggaaacta ggagtcgttt tcactgacaa ctccttcctc    14160
tacctagcct ggtatatgac tatgtctgtt cttggacact ataacaactt ttttttttgcc    14220 gctcaccttc tcgacattgc tatgggattc aagacattaa gaaccatctt gtcctcagta    14280
actcacaatg gcaaacagct cgtattaacc gttggcttat tagctgttgt tgtataccta    14340
tacactgtgg tggcattcaa tttttttccga aaattctaca ataaaagtga agatggtgat    14400
acaccagata tgaaatgtga cgatatgcta acatgctata tgttccacat gtatgttgga    14460
gttcgtgctg aggagggat cggggatgaa atcgaagacc cagcaggaga tgaatatgag    14520
atctatcgaa tcatctttga catcactttc ttcttctttg ttattgtcat tctcttggcc    14580
ataatacaag gtctaattat tgatgctttt ggagaactaa gagaccaaca ggaacaagtc    14640
aaagaagaca tggagaccaa atgcttcatc tgtgggatag caatgatta cttcgacaca    14700 gtgccacatg gctttgaaac ccacacttta caggagcaca acttggctaa ttacttgttt    14760
tttctgatgt atcttataaa caaagatgaa acagaacaca caggacagga atcttatgtc    14820
tggaagatgt atcaagaaag gtgttgggaa ttttcccag caggggattg cttccggaaa    14880
cagtatgaag accagctaaa ttaa                                           14904
```

<210> SEQ ID NO 2
<211> LENGTH: 53
<212> TYPE: RNA

<213> ORGANISM: Homo sapiens

<400> SEQUENCE: 2
auuugccuau agaguccgua agccuaaguc ugcaggaucu cauuggcuac uuc    53

<210> SEQ ID NO 3
<211> LENGTH: 53
<212> TYPE: RNA
<213> ORGANISM: Homo sapiens

<400> SEQUENCE: 3
auuugccuau agaguccgua agucuaaguc ugcaggaucu cauuggcuac uuc    53

<210> SEQ ID NO 4
<211> LENGTH: 21
<212> TYPE: RNA
<213> ORGANISM: Homo sapiens

<400> SEQUENCE: 4
aagucuaagu cugcaggauc u                                       21

<210> SEQ ID NO 5
<211> LENGTH: 21
<212> TYPE: RNA
<213> ORGANISM: Homo sapiens

<400> SEQUENCE: 5
uaagucuaag ucugcaggau c                                       21

<210> SEQ ID NO 6
<211> LENGTH: 21
<212> TYPE: RNA
<213> ORGANISM: Homo sapiens

<400> SEQUENCE: 6
guaagucuaa gucugcagga u                                       21

<210> SEQ ID NO 7
<211> LENGTH: 21
<212> TYPE: RNA
<213> ORGANISM: Homo sapiens

<400> SEQUENCE: 7
cguaagucua agucugcagg a                                       21

<210> SEQ ID NO 8
<211> LENGTH: 21
<212> TYPE: RNA
<213> ORGANISM: Homo sapiens

<400> SEQUENCE: 8
ccguaagucu aagucugcag g                                       21

<210> SEQ ID NO 9
<211> LENGTH: 21
<212> TYPE: RNA
<213> ORGANISM: Homo sapiens

<400> SEQUENCE: 9
uccguaaguc uaagucugca g                                       21

<210> SEQ ID NO 10
<211> LENGTH: 21

-continued

```
<212> TYPE: RNA
<213> ORGANISM: Homo sapiens

<400> SEQUENCE: 10
guccguaagu cuaagucugc a                                              21

<210> SEQ ID NO 11
<211> LENGTH: 21
<212> TYPE: RNA
<213> ORGANISM: Homo sapiens

<400> SEQUENCE: 11
aguccguaag ucuaagucug c                                              21

<210> SEQ ID NO 12
<211> LENGTH: 21
<212> TYPE: RNA
<213> ORGANISM: Homo sapiens

<400> SEQUENCE: 12
gaguccguaa gucuaagucu g                                              21

<210> SEQ ID NO 13
<211> LENGTH: 21
<212> TYPE: RNA
<213> ORGANISM: Homo sapiens

<400> SEQUENCE: 13
agaguccgua agucuaaguc u                                              21

<210> SEQ ID NO 14
<211> LENGTH: 21
<212> TYPE: RNA
<213> ORGANISM: Homo sapiens

<400> SEQUENCE: 14
uagaguccgu aagucuaagu c                                              21

<210> SEQ ID NO 15
<211> LENGTH: 21
<212> TYPE: RNA
<213> ORGANISM: Homo sapiens

<400> SEQUENCE: 15
auagaguccg uaagucuaag u                                              21

<210> SEQ ID NO 16
<211> LENGTH: 21
<212> TYPE: RNA
<213> ORGANISM: Homo sapiens

<400> SEQUENCE: 16
uauagagucc guaagucuaa g                                              21

<210> SEQ ID NO 17
<211> LENGTH: 21
<212> TYPE: RNA
<213> ORGANISM: Homo sapiens

<400> SEQUENCE: 17
cuauagaguc cguaagucua a                                              21

<210> SEQ ID NO 18
```

```
<211> LENGTH: 21
<212> TYPE: RNA
<213> ORGANISM: Homo sapiens

<400> SEQUENCE: 18
ccuauagagu ccguaagucu a                                              21

<210> SEQ ID NO 19
<211> LENGTH: 53
<212> TYPE: RNA
<213> ORGANISM: Homo sapiens

<400> SEQUENCE: 19
auuugccuau agagccgua agccuaaguc ugcaggaucu cauuggcuac uuc            53

<210> SEQ ID NO 20
<211> LENGTH: 53
<212> TYPE: RNA
<213> ORGANISM: Homo sapiens

<400> SEQUENCE: 20
auuugccuau agagccgua agucuaaguc ugcaggaucu cauuggcuac uuc            53

<210> SEQ ID NO 21
<211> LENGTH: 21
<212> TYPE: RNA
<213> ORGANISM: Homo sapiens

<400> SEQUENCE: 21
aagccuaagu cugcaggauc u                                              21

<210> SEQ ID NO 22
<211> LENGTH: 21
<212> TYPE: RNA
<213> ORGANISM: Homo sapiens

<400> SEQUENCE: 22
uaagccuaag ucugcaggau c                                              21

<210> SEQ ID NO 23
<211> LENGTH: 21
<212> TYPE: RNA
<213> ORGANISM: Homo sapiens

<400> SEQUENCE: 23
guaagccuaa gucugcagga u                                              21

<210> SEQ ID NO 24
<211> LENGTH: 21
<212> TYPE: RNA
<213> ORGANISM: Homo sapiens

<400> SEQUENCE: 24
cguaagccua agucugcagg a                                              21

<210> SEQ ID NO 25
<211> LENGTH: 21
<212> TYPE: RNA
<213> ORGANISM: Homo sapiens

<400> SEQUENCE: 25
ccguaagccu aagucugcag g                                              21
```

```
<210> SEQ ID NO 26
<211> LENGTH: 21
<212> TYPE: RNA
<213> ORGANISM: Homo sapiens

<400> SEQUENCE: 26
uccguaagcc uaagucugca g                                      21

<210> SEQ ID NO 27
<211> LENGTH: 21
<212> TYPE: RNA
<213> ORGANISM: Homo sapiens

<400> SEQUENCE: 27
guccguaagc cuaagucugc a                                      21

<210> SEQ ID NO 28
<211> LENGTH: 21
<212> TYPE: RNA
<213> ORGANISM: Homo sapiens

<400> SEQUENCE: 28
aguccguaag ccuaagucug c                                      21

<210> SEQ ID NO 29
<211> LENGTH: 21
<212> TYPE: RNA
<213> ORGANISM: Homo sapiens

<400> SEQUENCE: 29
gaguccguaa gccuaagucu g                                      21

<210> SEQ ID NO 30
<211> LENGTH: 21
<212> TYPE: RNA
<213> ORGANISM: Homo sapiens

<400> SEQUENCE: 30
agaguccgua agccuaaguc u                                      21

<210> SEQ ID NO 31
<211> LENGTH: 21
<212> TYPE: RNA
<213> ORGANISM: Homo sapiens

<400> SEQUENCE: 31
uagaguccgu aagccuaagu c                                      21

<210> SEQ ID NO 32
<211> LENGTH: 21
<212> TYPE: RNA
<213> ORGANISM: Homo sapiens

<400> SEQUENCE: 32
auagaguccg uaagccuaag u                                      21

<210> SEQ ID NO 33
<211> LENGTH: 21
<212> TYPE: RNA
<213> ORGANISM: Homo sapiens

<400> SEQUENCE: 33
uauagagucc guaagccuaa g                                      21
```

```
<210> SEQ ID NO 34
<211> LENGTH: 21
<212> TYPE: RNA
<213> ORGANISM: Homo sapiens

<400> SEQUENCE: 34
cuauagaguc cguaagccua a                                              21

<210> SEQ ID NO 35
<211> LENGTH: 21
<212> TYPE: RNA
<213> ORGANISM: Homo sapiens

<400> SEQUENCE: 35
ccuauagagu ccguaagccu a                                              21

<210> SEQ ID NO 36
<211> LENGTH: 42
<212> TYPE: RNA
<213> ORGANISM: Homo sapiens

<400> SEQUENCE: 36
gauguuccau uauuaaauga acacgcaaag augccucuua aa                       42

<210> SEQ ID NO 37
<211> LENGTH: 42
<212> TYPE: RNA
<213> ORGANISM: Homo sapiens

<400> SEQUENCE: 37
gauguuccau uauuaaauga acaugcaaag augccucuua aa                       42

<210> SEQ ID NO 38
<211> LENGTH: 21
<212> TYPE: RNA
<213> ORGANISM: Homo sapiens

<400> SEQUENCE: 38
acaugcaaag augccucuua a                                              21

<210> SEQ ID NO 39
<211> LENGTH: 21
<212> TYPE: RNA
<213> ORGANISM: Homo sapiens

<400> SEQUENCE: 39
aacaugcaaa gaugccucuu a                                              21

<210> SEQ ID NO 40
<211> LENGTH: 21
<212> TYPE: RNA
<213> ORGANISM: Homo sapiens

<400> SEQUENCE: 40
gaacaugcaa agaugccucu u                                              21

<210> SEQ ID NO 41
<211> LENGTH: 21
<212> TYPE: RNA
<213> ORGANISM: Homo sapiens

<400> SEQUENCE: 41
ugaacaugca aagaugccuc u                                              21
```

```
<210> SEQ ID NO 42
<211> LENGTH: 21
<212> TYPE: RNA
<213> ORGANISM: Homo sapiens

<400> SEQUENCE: 42
augaacaugc aaagaugccu c                                              21

<210> SEQ ID NO 43
<211> LENGTH: 21
<212> TYPE: RNA
<213> ORGANISM: Homo sapiens

<400> SEQUENCE: 43
aaugaacaug caaagaugcc u                                              21

<210> SEQ ID NO 44
<211> LENGTH: 21
<212> TYPE: RNA
<213> ORGANISM: Homo sapiens

<400> SEQUENCE: 44
aaaugaacau gcaaagaugc c                                              21

<210> SEQ ID NO 45
<211> LENGTH: 21
<212> TYPE: RNA
<213> ORGANISM: Homo sapiens

<400> SEQUENCE: 45
uaaaugaaca ugcaaagaug c                                              21

<210> SEQ ID NO 46
<211> LENGTH: 21
<212> TYPE: RNA
<213> ORGANISM: Homo sapiens

<400> SEQUENCE: 46
uuaaaugaac augcaaagau g                                              21

<210> SEQ ID NO 47
<211> LENGTH: 21
<212> TYPE: RNA
<213> ORGANISM: Homo sapiens

<400> SEQUENCE: 47
auuaaaugaa caugcaaaga u                                              21

<210> SEQ ID NO 48
<211> LENGTH: 21
<212> TYPE: RNA
<213> ORGANISM: Homo sapiens

<400> SEQUENCE: 48
uauuaaauga acaugcaaag a                                              21

<210> SEQ ID NO 49
<211> LENGTH: 21
<212> TYPE: RNA
<213> ORGANISM: Homo sapiens
```

```
<400> SEQUENCE: 49
uuauuaaaug aacaugcaaa g                                              21

<210> SEQ ID NO 50
<211> LENGTH: 21
<212> TYPE: RNA
<213> ORGANISM: Homo sapiens

<400> SEQUENCE: 50
auuauuaaau gaacaugcaa a                                              21

<210> SEQ ID NO 51
<211> LENGTH: 21
<212> TYPE: RNA
<213> ORGANISM: Homo sapiens

<400> SEQUENCE: 51
cauuauuaaa ugaacaugca a                                              21

<210> SEQ ID NO 52
<211> LENGTH: 21
<212> TYPE: RNA
<213> ORGANISM: Homo sapiens

<400> SEQUENCE: 52
ccauuauuaa augaacaugc a                                              21

<210> SEQ ID NO 53
<211> LENGTH: 42
<212> TYPE: RNA
<213> ORGANISM: Homo sapiens

<400> SEQUENCE: 53
gauguuccau uauuaaauga acacgcaaag augccucuua aa                       42

<210> SEQ ID NO 54
<211> LENGTH: 42
<212> TYPE: RNA
<213> ORGANISM: Homo sapiens

<400> SEQUENCE: 54
gauguuccau uauuaaauga acaugcaaag augccucuua aa                       42

<210> SEQ ID NO 55
<211> LENGTH: 21
<212> TYPE: RNA
<213> ORGANISM: Homo sapiens

<400> SEQUENCE: 55
acacgcaaag augccucuua a                                              21

<210> SEQ ID NO 56
<211> LENGTH: 21
<212> TYPE: RNA
<213> ORGANISM: Homo sapiens

<400> SEQUENCE: 56
aacacgcaaa gaugccucuu a                                              21

<210> SEQ ID NO 57
<211> LENGTH: 21
<212> TYPE: RNA
```

<213> ORGANISM: Homo sapiens

<400> SEQUENCE: 57
gaacacgcaa agaugccucu u                                           21

<210> SEQ ID NO 58
<211> LENGTH: 21
<212> TYPE: RNA
<213> ORGANISM: Homo sapiens

<400> SEQUENCE: 58
ugaacacgca aagaugccuc u                                           21

<210> SEQ ID NO 59
<211> LENGTH: 21
<212> TYPE: RNA
<213> ORGANISM: Homo sapiens

<400> SEQUENCE: 59
augaacacgc aaagaugccu c                                           21

<210> SEQ ID NO 60
<211> LENGTH: 21
<212> TYPE: RNA
<213> ORGANISM: Homo sapiens

<400> SEQUENCE: 60
aaugaacacg caaagaugcc u                                           21

<210> SEQ ID NO 61
<211> LENGTH: 21
<212> TYPE: RNA
<213> ORGANISM: Homo sapiens

<400> SEQUENCE: 61
aaaugaacac gcaaagaugc c                                           21

<210> SEQ ID NO 62
<211> LENGTH: 21
<212> TYPE: RNA
<213> ORGANISM: Homo sapiens

<400> SEQUENCE: 62
uaaaugaaca cgcaaagaug c                                           21

<210> SEQ ID NO 63
<211> LENGTH: 21
<212> TYPE: RNA
<213> ORGANISM: Homo sapiens

<400> SEQUENCE: 63
uuaaaugaac acgcaaagau g                                           21

<210> SEQ ID NO 64
<211> LENGTH: 21
<212> TYPE: RNA
<213> ORGANISM: Homo sapiens

<400> SEQUENCE: 64
auuaaaugaa cacgcaaaga u                                           21

<210> SEQ ID NO 65
<211> LENGTH: 21

```
<212> TYPE: RNA
<213> ORGANISM: Homo sapiens

<400> SEQUENCE: 65
uauuaaauga acacgcaaag a                                         21

<210> SEQ ID NO 66
<211> LENGTH: 21
<212> TYPE: RNA
<213> ORGANISM: Homo sapiens

<400> SEQUENCE: 66
uuauuaaaug aacacgcaaa g                                         21

<210> SEQ ID NO 67
<211> LENGTH: 21
<212> TYPE: RNA
<213> ORGANISM: Homo sapiens

<400> SEQUENCE: 67
auuauuaaau gaacacgcaa a                                         21

<210> SEQ ID NO 68
<211> LENGTH: 21
<212> TYPE: RNA
<213> ORGANISM: Homo sapiens

<400> SEQUENCE: 68
cauuauuaaa ugaacacgca a                                         21

<210> SEQ ID NO 69
<211> LENGTH: 21
<212> TYPE: RNA
<213> ORGANISM: Homo sapiens

<400> SEQUENCE: 69
ccauuauuaa augaacacgc a                                         21

<210> SEQ ID NO 70
<211> LENGTH: 45
<212> TYPE: RNA
<213> ORGANISM: Homo sapiens

<400> SEQUENCE: 70
ggagaacauu ucccuuauga acaagaaauc aaguucuuug caaaa               45

<210> SEQ ID NO 71
<211> LENGTH: 45
<212> TYPE: RNA
<213> ORGANISM: Homo sapiens

<400> SEQUENCE: 71
ggagaacauu ucccuuauga acgagaaauc aaguucuuug caaaa               45

<210> SEQ ID NO 72
<211> LENGTH: 21
<212> TYPE: RNA
<213> ORGANISM: Homo sapiens

<400> SEQUENCE: 72
aacgagaaau caaguucuuu g                                         21

<210> SEQ ID NO 73
```

-continued

```
<211> LENGTH: 21
<212> TYPE: RNA
<213> ORGANISM: Homo sapiens

<400> SEQUENCE: 73
gaacgagaaa ucaaguucuu u                                              21

<210> SEQ ID NO 74
<211> LENGTH: 21
<212> TYPE: RNA
<213> ORGANISM: Homo sapiens

<400> SEQUENCE: 74
ugaacgagaa aucaaguucu u                                              21

<210> SEQ ID NO 75
<211> LENGTH: 21
<212> TYPE: RNA
<213> ORGANISM: Homo sapiens

<400> SEQUENCE: 75
augaacgaga aaucaaguuc u                                              21

<210> SEQ ID NO 76
<211> LENGTH: 21
<212> TYPE: RNA
<213> ORGANISM: Homo sapiens

<400> SEQUENCE: 76
uaugaacgag aaaucaaguu c                                              21

<210> SEQ ID NO 77
<211> LENGTH: 21
<212> TYPE: RNA
<213> ORGANISM: Homo sapiens

<400> SEQUENCE: 77
uuaugaacga gaaaucaagu u                                              21

<210> SEQ ID NO 78
<211> LENGTH: 21
<212> TYPE: RNA
<213> ORGANISM: Homo sapiens

<400> SEQUENCE: 78
cuuaugaacg agaaaucaag u                                              21

<210> SEQ ID NO 79
<211> LENGTH: 21
<212> TYPE: RNA
<213> ORGANISM: Homo sapiens

<400> SEQUENCE: 79
ccuuaugaac gagaaaucaa g                                              21

<210> SEQ ID NO 80
<211> LENGTH: 21
<212> TYPE: RNA
<213> ORGANISM: Homo sapiens

<400> SEQUENCE: 80
cccuuaugaa cgagaaauca a                                              21
```

```
<210> SEQ ID NO 81
<211> LENGTH: 21
<212> TYPE: RNA
<213> ORGANISM: Homo sapiens

<400> SEQUENCE: 81
ucccuuauga acgagaaauc a                                              21

<210> SEQ ID NO 82
<211> LENGTH: 21
<212> TYPE: RNA
<213> ORGANISM: Homo sapiens

<400> SEQUENCE: 82
uucccuuaug aacgagaaau c                                              21

<210> SEQ ID NO 83
<211> LENGTH: 21
<212> TYPE: RNA
<213> ORGANISM: Homo sapiens

<400> SEQUENCE: 83
uuucccuuau gaacgagaaa u                                              21

<210> SEQ ID NO 84
<211> LENGTH: 21
<212> TYPE: RNA
<213> ORGANISM: Homo sapiens

<400> SEQUENCE: 84
auuucccuua ugaacgagaa a                                              21

<210> SEQ ID NO 85
<211> LENGTH: 21
<212> TYPE: RNA
<213> ORGANISM: Homo sapiens

<400> SEQUENCE: 85
cauuucccuu augaacgaga a                                              21

<210> SEQ ID NO 86
<211> LENGTH: 21
<212> TYPE: RNA
<213> ORGANISM: Homo sapiens

<400> SEQUENCE: 86
acauuucccu uaugaacgag a                                              21

<210> SEQ ID NO 87
<211> LENGTH: 45
<212> TYPE: RNA
<213> ORGANISM: Homo sapiens

<400> SEQUENCE: 87
ggagaacauu ucccuuauga acaagaaauc aaguucuuug caaaa                    45

<210> SEQ ID NO 88
<211> LENGTH: 45
<212> TYPE: RNA
<213> ORGANISM: Homo sapiens

<400> SEQUENCE: 88
ggagaacauu ucccuuauga acgagaaauc aaguucuuug caaaa                    45
```

```
<210> SEQ ID NO 89
<211> LENGTH: 21
<212> TYPE: RNA
<213> ORGANISM: Homo sapiens

<400> SEQUENCE: 89
aacaagaaau caaguucuuu g                                              21

<210> SEQ ID NO 90
<211> LENGTH: 21
<212> TYPE: RNA
<213> ORGANISM: Homo sapiens

<400> SEQUENCE: 90
gaacaagaaa ucaaguucuu u                                              21

<210> SEQ ID NO 91
<211> LENGTH: 21
<212> TYPE: RNA
<213> ORGANISM: Homo sapiens

<400> SEQUENCE: 91
ugaacaagaa aucaaguucu u                                              21

<210> SEQ ID NO 92
<211> LENGTH: 21
<212> TYPE: RNA
<213> ORGANISM: Homo sapiens

<400> SEQUENCE: 92
augaacaaga aaucaaguuc u                                              21

<210> SEQ ID NO 93
<211> LENGTH: 21
<212> TYPE: RNA
<213> ORGANISM: Homo sapiens

<400> SEQUENCE: 93
uaugaacaag aaaucaaguu c                                              21

<210> SEQ ID NO 94
<211> LENGTH: 21
<212> TYPE: RNA
<213> ORGANISM: Homo sapiens

<400> SEQUENCE: 94
uuaugaacaa gaaaucaagu u                                              21

<210> SEQ ID NO 95
<211> LENGTH: 21
<212> TYPE: RNA
<213> ORGANISM: Homo sapiens

<400> SEQUENCE: 95
cuuaugaaca agaaaucaag u                                              21

<210> SEQ ID NO 96
<211> LENGTH: 21
<212> TYPE: RNA
<213> ORGANISM: Homo sapiens

<400> SEQUENCE: 96
ccuuaugaac aagaaaucaa g                                              21
```

<210> SEQ ID NO 97
<211> LENGTH: 21
<212> TYPE: RNA
<213> ORGANISM: Homo sapiens

<400> SEQUENCE: 97
cccuuaugaa caagaaauca a                                              21

<210> SEQ ID NO 98
<211> LENGTH: 21
<212> TYPE: RNA
<213> ORGANISM: Homo sapiens

<400> SEQUENCE: 98
ucccuuauga acaagaaauc a                                              21

<210> SEQ ID NO 99
<211> LENGTH: 21
<212> TYPE: RNA
<213> ORGANISM: Homo sapiens

<400> SEQUENCE: 99
uucccuuaug aacaagaaau c                                              21

<210> SEQ ID NO 100
<211> LENGTH: 21
<212> TYPE: RNA
<213> ORGANISM: Homo sapiens

<400> SEQUENCE: 100
uuucccuuau gaacaagaaa u                                              21

<210> SEQ ID NO 101
<211> LENGTH: 21
<212> TYPE: RNA
<213> ORGANISM: Homo sapiens

<400> SEQUENCE: 101
auuucccuua ugaacaagaa a                                              21

<210> SEQ ID NO 102
<211> LENGTH: 21
<212> TYPE: RNA
<213> ORGANISM: Homo sapiens

<400> SEQUENCE: 102
cauuucccuu augaacaaga a                                              21

<210> SEQ ID NO 103
<211> LENGTH: 21
<212> TYPE: RNA
<213> ORGANISM: Homo sapiens

<400> SEQUENCE: 103
acauuucccu uaugaacaag a                                              21

<210> SEQ ID NO 104
<211> LENGTH: 21
<212> TYPE: RNA
<213> ORGANISM: Homo sapiens -continued

```
<400> SEQUENCE: 104
aacauuuccc uuaugaacaa g                                     21

<210> SEQ ID NO 105
<211> LENGTH: 56
<212> TYPE: DNA
<213> ORGANISM: Homo sapiens

<400> SEQUENCE: 105
aacagaagct gctgaactat tttgctcgca acttttacaa catgagaatg ctggcc     56

<210> SEQ ID NO 106
<211> LENGTH: 56
<212> TYPE: DNA
<213> ORGANISM: Homo sapiens

<400> SEQUENCE: 106
aacagaagct gctgaactat tttgcttgca acttttacaa catgagaatg ctggcc     56

<210> SEQ ID NO 107
<211> LENGTH: 21
<212> TYPE: RNA
<213> ORGANISM: Homo sapiens

<400> SEQUENCE: 107
ugcuugcaac uuuuacaaca u                                     21

<210> SEQ ID NO 108
<211> LENGTH: 21
<212> TYPE: RNA
<213> ORGANISM: Homo sapiens

<400> SEQUENCE: 108
uugcuugcaa cuuuuacaac a                                     21

<210> SEQ ID NO 109
<211> LENGTH: 21
<212> TYPE: RNA
<213> ORGANISM: Homo sapiens

<400> SEQUENCE: 109
uuugcuugca cuuuuacaa c                                      21

<210> SEQ ID NO 110
<211> LENGTH: 21
<212> TYPE: RNA
<213> ORGANISM: Homo sapiens

<400> SEQUENCE: 110
uuuugcuugc aacuuuuaca a                                     21

<210> SEQ ID NO 111
<211> LENGTH: 21
<212> TYPE: RNA
<213> ORGANISM: Homo sapiens

<400> SEQUENCE: 111
auuuugcuug caacuuuuac a                                     21

<210> SEQ ID NO 112
<211> LENGTH: 21
<212> TYPE: RNA
```

```
<213> ORGANISM: Homo sapiens

<400> SEQUENCE: 112
uauuuugcuu gcaacuuuua c                                              21

<210> SEQ ID NO 113
<211> LENGTH: 21
<212> TYPE: RNA
<213> ORGANISM: Homo sapiens

<400> SEQUENCE: 113
cuauuuugcu ugcaacuuuu a                                              21

<210> SEQ ID NO 114
<211> LENGTH: 21
<212> TYPE: RNA
<213> ORGANISM: Homo sapiens

<400> SEQUENCE: 114
acuauuuugc uugcaacuuu u                                              21

<210> SEQ ID NO 115
<211> LENGTH: 21
<212> TYPE: RNA
<213> ORGANISM: Homo sapiens

<400> SEQUENCE: 115
aacuauuuug cuugcaacuu u                                              21

<210> SEQ ID NO 116
<211> LENGTH: 21
<212> TYPE: RNA
<213> ORGANISM: Homo sapiens

<400> SEQUENCE: 116
gaacuauuuu gcuugcaacu u                                              21

<210> SEQ ID NO 117
<211> LENGTH: 21
<212> TYPE: RNA
<213> ORGANISM: Homo sapiens

<400> SEQUENCE: 117
ugaacuauuu ugcuugcaac u                                              21

<210> SEQ ID NO 118
<211> LENGTH: 21
<212> TYPE: RNA
<213> ORGANISM: Homo sapiens

<400> SEQUENCE: 118
cugaacuauu uugcuugcaa c                                              21

<210> SEQ ID NO 119
<211> LENGTH: 21
<212> TYPE: RNA
<213> ORGANISM: Homo sapiens

<400> SEQUENCE: 119
gcugaacuau uuugcuugca a                                              21

<210> SEQ ID NO 120
<211> LENGTH: 22
```

```
<212> TYPE: DNA
<213> ORGANISM: Artificial Sequence
<220> FEATURE:
<223> OTHER INFORMATION: synthetic oligonucleotide

<400> SEQUENCE: 120
ctatatcatg gccgacaagc ag                                           22

<210> SEQ ID NO 121
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 121
gcgtgatgaa cttcgaggac g                                            21

<210> SEQ ID NO 122
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 122
gctcgtccat gccgagcgtg                                              20

<210> SEQ ID NO 123
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 123
cagcccatgg tcttcttctg c                                            21

<210> SEQ ID NO 124
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 124
gaacctccag cgatactgc                                               19

<210> SEQ ID NO 125
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 125
ctggtaccct tgtcatcgtc atccttgtaa tcg                               33

<210> SEQ ID NO 126
<211> LENGTH: 29
<212> TYPE: DNA
<213> ORGANISM: Artificial Sequence
<220> FEATURE:
<223> OTHER INFORMATION: synthetic oligonucleotide
```

```
<400> SEQUENCE: 126
ctggtaacct attaagcgta gtcaggtac                                         29

<210> SEQ ID NO 127
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 127
aaatcccatc accatcttcc                                                   20

<210> SEQ ID NO 128
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 128
ggttcacacc catgacgaac                                                   20

<210> SEQ ID NO 129
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 129
tgctgtaaaa gttgcaagca aaatagtttt g                                      31

<210> SEQ ID NO 130
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 130
gccactgact gactattttg cgcaactttt ac                                     32

<210> SEQ ID NO 131
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 131
cctggtaaaa gttgcgcaaa atagtcagtc a                                      31

<210> SEQ ID NO 132
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 132
gtggccaaaa ctattttgct tgcaactttt ac                                     32

<210> SEQ ID NO 133
```

```
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 133
tagctagctg cttcgcgatg tacgg                                          25

<210> SEQ ID NO 134
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 134
gtgaattcga acaaacgacc caacacccg                                      29
```